United States Patent
Shinohara et al.

(10) Patent No.: US 10,800,758 B2
(45) Date of Patent: Oct. 13, 2020

(54) PYRIMIDINE COMPOUND

(71) Applicant: OTSUKA PHARMACEUTICAL CO., LTD., Tokyo (JP)

(72) Inventors: Tomoichi Shinohara, Naruto (JP); Shin Iwata, Tokushima (JP); Kenta Arai, Tokushima (JP); Nobuaki Ito, Tokushima (JP); Masaki Suzuki, Itano-gun (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/471,998

(22) PCT Filed: May 31, 2018

(86) PCT No.: PCT/JP2018/020997
§ 371 (c)(1),
(2) Date: Jun. 20, 2019

(87) PCT Pub. No.: WO2018/221667
PCT Pub. Date: Dec. 6, 2018

(65) Prior Publication Data
US 2020/0017476 A1    Jan. 16, 2020

(30) Foreign Application Priority Data
May 31, 2017    (WO) ............... PCT/JP2017/020322

(51) Int. Cl.
*C07D 403/04*    (2006.01)
*C07D 401/14*    (2006.01)
*C07F 7/08*    (2006.01)
*A61P 25/08*    (2006.01)

(52) U.S. Cl.
CPC ......... *C07D 403/04* (2013.01); *A61P 25/08* (2018.01); *C07D 401/14* (2013.01); *C07F 7/0812* (2013.01)

(58) Field of Classification Search
CPC ... C07D 403/04; C07D 401/14; C07F 7/0812; A61P 25/08
See application file for complete search history.

(56) References Cited

FOREIGN PATENT DOCUMENTS

| | | |
|---|---|---|
| JP | 2013-513564 A | 4/2013 |
| JP | 2013-518046 A | 5/2013 |
| JP | 2014-521651 A | 8/2014 |
| WO | 2004/009559 A2 | 1/2004 |
| WO | 2011/069951 A1 | 6/2011 |
| WO | WO 2011/069951 * 6/2011 ........... C07D 233/76 |
| WO | 2011/091153 A1 | 7/2011 |
| WO | 2012/076877 A1 | 6/2012 |
| WO | 2012/168710 A1 | 12/2012 |
| WO | 2013/016488 A1 | 1/2013 |
| WO | 2013/083994 A1 | 6/2013 |
| WO | 2017/098254 A1 | 6/2017 |

OTHER PUBLICATIONS

Office Action issued in Japanese Application No. 2019-535398 dated Apr. 21, 2020; 7 pages total.
International Preliminary Report on Patentability and Written Opinion of the International Searching Authority for corresponding PCT Application No. PCT/JP2018/020997 dated Dec. 12, 2019.
International Preliminary Report on Patentability and Translation of Written Opinion of the International Searching Authority for priority PCT Application No. PCT/JP2017/020322 dated Dec. 12, 2019.
International Search Report dated Aug. 10, 2018 issued in corresponding PCT Application No. PCT/JP2018/020997.
International Search Report dated Aug. 22, 2017 issued in priority application No. PCT/JP2017/020322.

* cited by examiner

*Primary Examiner* — Erich A Leeser
(74) *Attorney, Agent, or Firm* — Sughrue Mion, PLLC

(57) ABSTRACT

The present invention provides a novel pyrimidine compound represented by Formula [I] and a salt thereof:

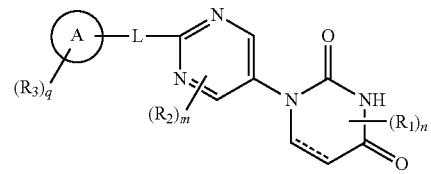

[in the formula, the symbols are as defined in the specification], which is useful for treating, preventing and/or diagnosing seizure and the like in disease involving epileptic seizure or convulsive seizure (including multiple drug resistant seizure, refractory seizure, acute symptomatic seizure, febrile seizure and status epilepticus), as well as a medical use therefor.

88 Claims, No Drawings

PYRIMIDINE COMPOUND

CROSS REFERENCE TO RELATED APPLICATIONS

This application is a National Stage of International Application No. PCT/JP2018/020997 filed May 31, 2018, claiming priority based on International Application No. PCT/JP2017/020322 filed May 31, 2017.

TECHNICAL FIELD

The present invention relates to a pyrimidine compound and a salt thereof. The present invention also relates to a medicament having a pyrimidine compound or a salt thereof as an active ingredient and useful for treating, preventing and/or diagnosing seizure and the like in disease involving epileptic seizure or convulsive seizure.

BACKGROUND ART

The prevalence of epilepsy is about 1% of the population. It is considered a common neurological disorder with about 1 million patients in Japan and a lifetime morbidity rate of 3% to 4%, and it is estimated that tens of thousands of people develop epilepsy every year. About 70% of these patients can control their seizure with existing antiepileptic drugs and pursue their everyday lives without problems, but the remaining 30% of epileptic patients are unable to adequately control their seizure, and are anxious that seizure may occur without warning. Most existing antiepileptic drugs are aimed to normalize the excitation/inhibition imbalances in neural activity by suppressing hyperexcitation and excessive synchronization of neuronal activity, but doses above the optimal dose may disturb the equilibrium of neuronal activity, and induce motor dysfunction and epileptic seizure.

PTL 1 discloses compounds having a pyrimidine in its structure as compounds for use in the treatment and the like of diseases or conditions requiring modulators of the Kv3.1 and/or Kv3.2 channel, including epilepsy.

PTL 2 and 3 disclose compounds having a pyrimidine skeleton as kynurenine-3-monooxygenase inhibitors for treating neurodegerenative conditions including epilepsy.

PTL 4 discloses uracil compounds as compounds exhibiting antiepileptic action.

However, no compound having a structure comprising the 5-position carbon of a pyrimidine bound to the 1-position nitrogen of a uracil skeleton is either disclosed or suggested in any patent literature.

CITATION LIST

Patent Literature

[PTL 1] WO 2011/069951
[PTL 2] WO 2013/016488
[PTL 3] WO 2011/091153
[PTL 4] WO 2004/009559

DISCLOSURE OF INVENTION

It is an object of the present invention to provide a novel pyrimidine compound or a salt thereof useful for treating, preventing and/or diagnosing seizure and the like in disease involving epileptic seizure or convulsive seizure, together with a medical use therefor.

It is another object of the present invention to provide a medicament having a wide treatment spectrum in comparison with existing antiepileptic drugs, whereby the balance of neuronal excitation/inhibition can be maintained even at doses that completely suppress epileptic seizure.

As a result of exhaustive research aimed at solving the aforementioned problems, the inventors succeeded in synthesizing a novel pyrimidine compound having a wide treatment spectrum in comparison with existing antiepileptic drugs. The present invention was perfected based on these findings.

That is, the present invention includes the following embodiments.

[1] A compound represented by Formula [I]:

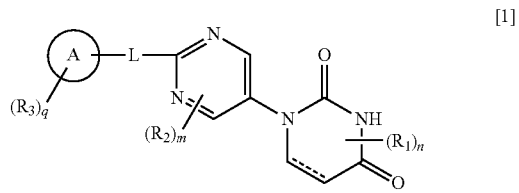

wherein
ring A is phenyl, naphthyl or pyridyl;
$R_1$ is lower alkyl;
$R_2$ is —O-lower alkyl;
$R_3$ is halogen, lower alkynyl, lower alkyl optionally substituted with halogen, —O-lower alkyl optionally substituted with deuterium or halogen, —S-lower alkyl optionally substituted with halogen, phenyl, pentafluorothio, —CN, —O-benzyl or —Si-mono-, di- or tri-lower alkyl wherein di or tri may be same or different alkyl;
L is bond, lower alkylene, —O— or —S—;
each of m and n is 0 or 1;
q is 0, 1 or 2, and when q is 2, each $R_3$ independently represents the same or different substituent; and
$\text{------}$ represents single or double bond, or a salt thereof.

[2] The compound or a salt thereof according to [1], wherein
ring A is phenyl,
L is —O—, and
n is 0.

[3] The compound or a salt thereof according to [1] or [2], wherein m is 0.

[4] The compound or a salt thereof according to any of [1] to [3], wherein $R_3$ is halogen, lower alkynyl, lower alkyl or —S-lower alkyl optionally substituted with halogen.

[5] The compound or a salt thereof according to any of [1] to [4], wherein

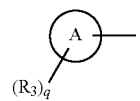

is phenyl, monohalophenyl, dihalophenyl, mono-lower alkynylphenyl or mono-lower alkylphenyl or phenyl substituted with one halogen and one lower alkyl group.

[6] A compound selected from the group consisting of the following compounds:
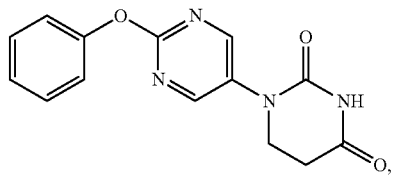
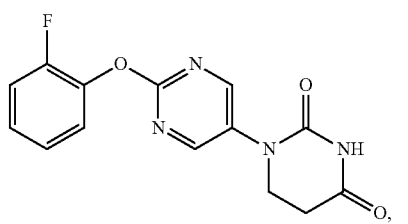
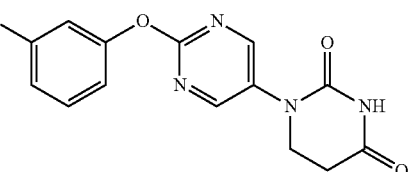
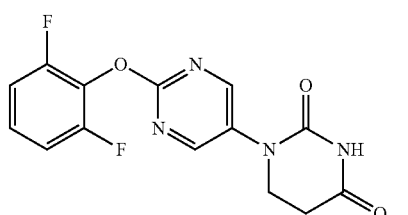
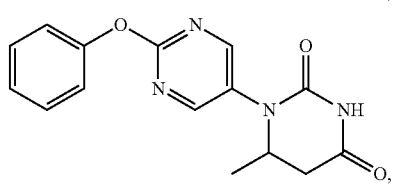
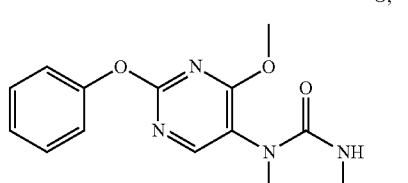
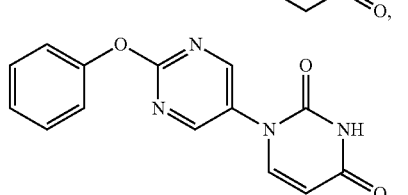
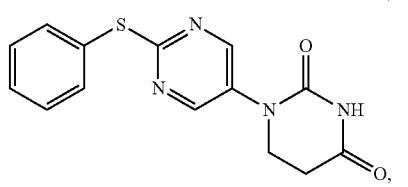
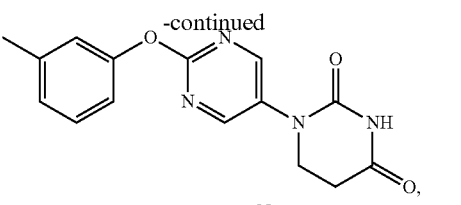
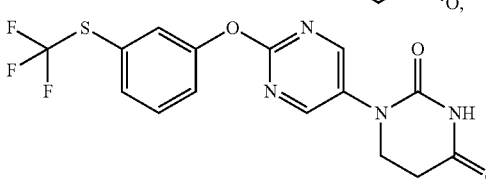
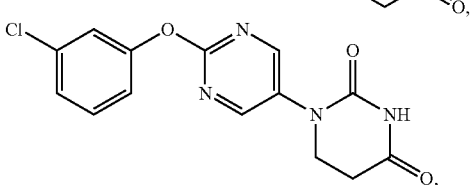
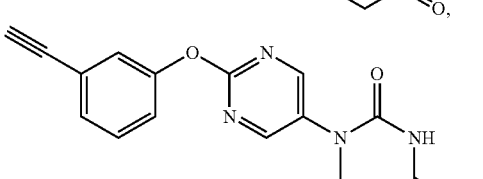
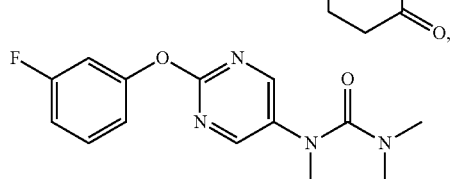
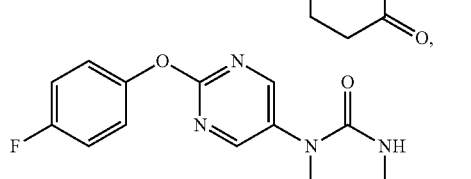
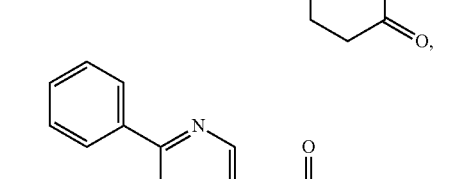
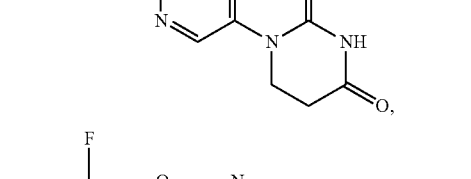
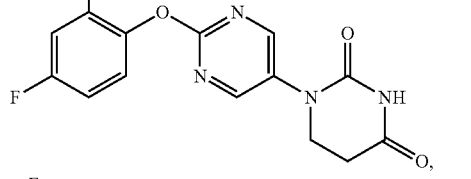
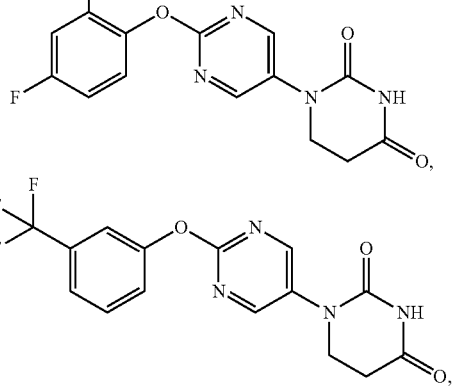

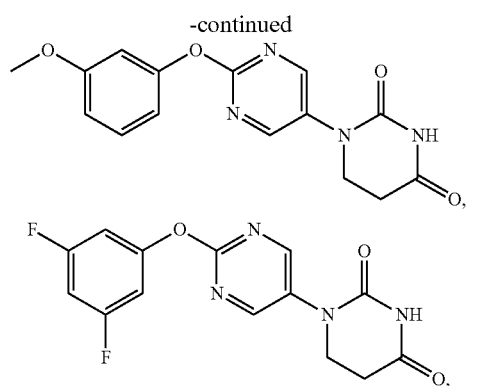
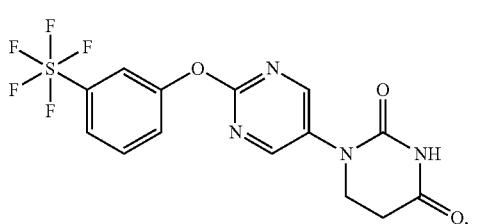
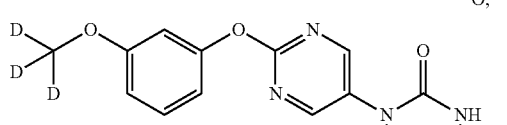
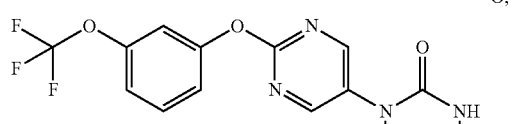
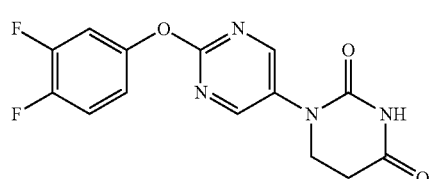
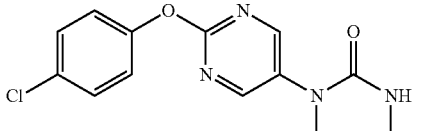
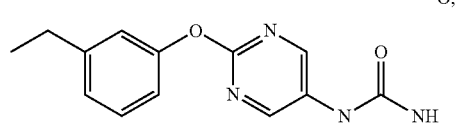
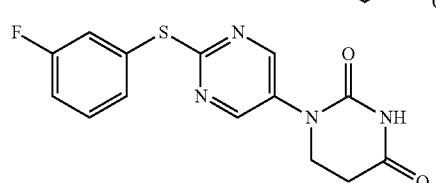
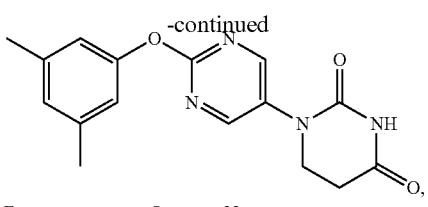
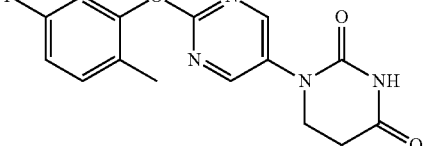
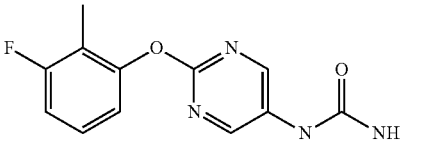
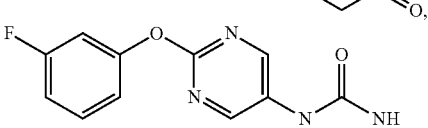
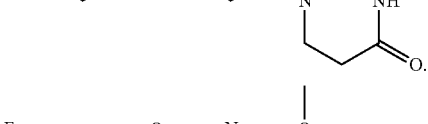
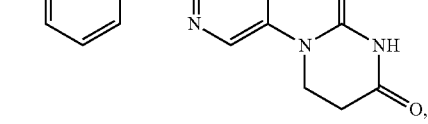
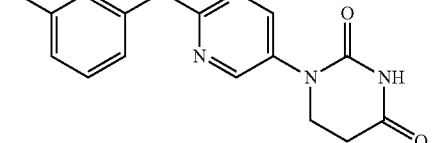
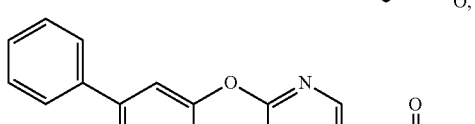
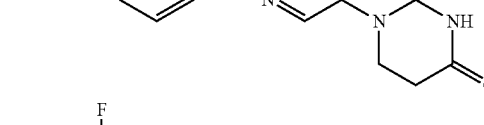
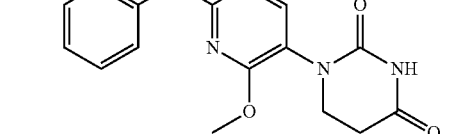
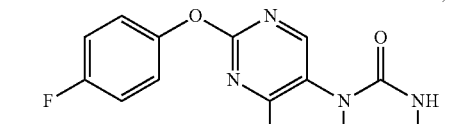
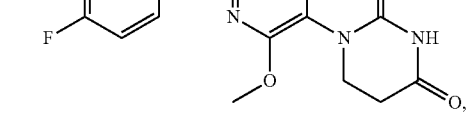

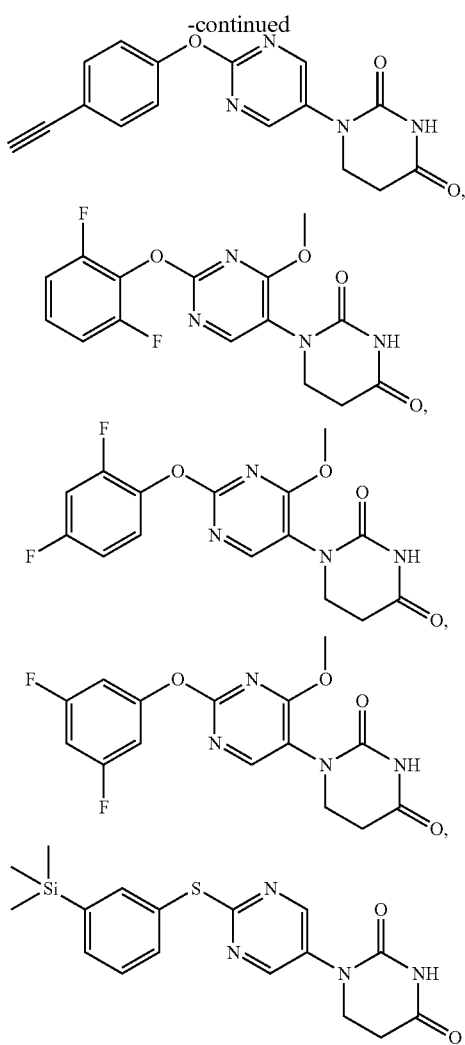

or a salt thereof.

[7] A pharmaceutical composition comprising a compound or a salt thereof according to any of [1] to [6] as an active ingredient and pharmaceutically acceptable carrier or excipient.

[8] A therapeutic, preventative and/or diagnostic agent for seizure in disease involving epileptic seizure or convulsive seizure (including multiple drug resistant seizure, refractory seizure, acute symptomatic seizure, febrile seizure and status epilepticus), comprising a compound or a salt thereof according to any of [1] to [6].

[9] The therapeutic, preventative or diagnostic agent according to [8], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[10] The therapeutic, preventative or diagnostic agent according to [8], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[11] A therapeutic, preventative and/or diagnostic pharmaceutical composition for seizure in disease involving epileptic seizure or convulsive seizure (including multiple drug resistant seizure, refractory seizure, acute symptomatic seizure, febrile seizure and status epilepticus), comprising a compound or a salt thereof according to any of [1] to [6] as an active ingredient.

[12] The composition according to [11], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizures of unknown onset including motor seizure (including tonic-clonic seizure and epileptic spasms) and non-motor seizure (including behavior arrest seizure).

[13] The composition according to [11], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[14] A method for treating, preventing and/or diagnosing seizure in disease involving epileptic seizure or convulsive seizure (including multiple drug resistant seizure, refractory seizure, acute symptomatic seizure, febrile seizure and status epilepticus), wherein comprising administering to a human in need thereof an effective amount of a compound or a salt thereof according to any of [1] to [6].

[15] The method according to [14], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[16] The method according to [14], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[17] A compound or a salt thereof according to any of [1] to [6] for use in the treatment, prevention and/or diagnosis of seizure in disease involving epileptic seizure or convulsive seizure (including multiple drug resistant seizure, refractory seizure, acute symptomatic seizure, febrile seizure and status epilepticus).

[18] The compound or a salt thereof according to [17], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonicseizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[19] The compound or a salt thereof according to [17], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[20] Use of a compound or a salt thereof according to any of [1] to [6] in the manufacture of a medicament for treating, preventing and/or diagnosing seizure in disease involving epileptic seizure or convulsive seizure (including multiple drug resistant seizure, refractory seizure, acute symptomatic seizure, febrile seizure and status epilepticus).

[21] The use according to [20], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[22] The use according to [20], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

The compound and a salt thereof of the present invention are highly effective for treating, preventing and/or diagnosing disease and the like involving epileptic seizure, convulsive seizure or the like. Moreover, the compound and a salt thereof of the present invention have excellent feature for use as active ingredient in pharmaceuticals, and for example have excellent feature such as few side effects, tolerability, stability (storage stability, metabolic stability, etc.) and the like. Furthermore, the compound and a salt thereof of the present invention have a wide treatment spectrum in comparison with existing antiepileptic drugs.

DESCRIPTION OF EMBODIMENTS

The phrases and terms used in this specification are explained in detail below.

The "lower alkyl" may be $C_{1-6}$ linear or branched alkyl, and specific examples include methyl, ethyl, propyl, isopropyl, butyl, isobutyl, sec-butyl, tert-butyl, pentyl, isopentyl, neopentyl, hexyl, isohexyl, 3-methylpentyl and the like. Lower alkyl having deuterium atoms substituted for 1 to 3 hydrogen atoms is also included.

The "halogen" is fluorine, chlorine, bromine or iodine, and fluorine, chlorine or iodine is preferred. Fluorine or chlorine is more preferred.

The "lower alkynyl" may be a $C_{2-6}$ linear or branched alkynyl, and specific examples include ethynyl, (1- or 2-)propynyl, 1-methyl-(1- or 2-)propynyl, 1-ethyl-(1- or 2-)propynyl, (1-, 2- or 3-)butynyl, (1-, 2-, 3- or 4-)pentynyl, (1-, 2-, 3-, 4- or 5-)hexynyl and the like.

Examples of the "lower alkyl optionally substituted with halogen" include $C_{1-6}$ linear or branched alkyl optionally substituted with 1 to 4 halogens, and specific examples include methyl, ethyl, n-propyl, isopropyl, n-butyl, isobutyl, tert-butyl, sec-butyl, n-pentyl, isopentyl, neopentyl, n-hexyl, isohexyl, 3-methylpentyl, fluoromethyl, chloromethyl, bromomethyl, iodomethyl, difluoromethyl, dichloromethyl, dibromomethyl, trifluoromethyl, trichloromethyl, 2-fluoroethyl, 2-chloroethyl, 2,2,2-trifluoroethyl, 2,2,2-trichloroethyl, 1,1,2,2-tetrafluoroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl and the like.

Examples of the "lower alkylene" include $C_{1-6}$ linear or branched alkylene, and specific examples include methylene, ethylene, 1-methylethylene, 2-methylethylene, trimethylene, 2-methyltrimethylene, 2,2-dimethyltrimethylene, 1-methyltrimethylene, methylmethylene, ethylmethylene, dimethylmethylene, tetramethylene, pentamethylene, hexamethylene and the like.

Each of the groups defined in this specification may be bound appropriately to another group via a linker such as —O—, —CO—, —COO—, —S—, —SO—, —SO$_2$—, —Si—, —O—CO— or the like.

The various substituents in the compound represented by General Formula [I] of the present invention (hereunder called "compound [I] of the present invention") are explained below.

The ring A in the compound [I] of the present invention is phenyl, naphthyl or pyridyl, and is preferably phenyl.

$R_1$ in the compound [I] of the present invention is lower alkyl, and is preferably a $C_{1-6}$ alkyl, or more preferably methyl or ethyl.

$R_2$ in the compound [I] of the present invention is —O-lower alkyl, and is preferably —O—$C_{1-6}$ alkyl, or more preferably methoxy.

$R_3$ in the compound [I] of the present invention is halogen, lower alkynyl, lower alkyl optionally substituted with halogen, —O-lower alkyl optionally substituted with deuterium or halogen, —S-lower alkyl optionally substituted with halogen, phenyl, pentafluorothio, —CN, —O-benzyl or —Si-mono-, di- or tri-lower alkyl wherein di or tri may be same or different alkyl, and is preferably halogen, lower alkynyl, lower alkyl or trifluoromethylthio, or more preferably fluorine, chlorine, ethynyl, methyl or trifluoromethylthio, or still more preferably fluorine, ethynyl or methyl.

L in the compound [I] of the present invention is bond, lower alkylene, —O— or —S—, and is preferably bond or —O—, or more preferably —O—.

n in the compound [I] of the present invention is 0 or 1, and is preferably 0.

m in the compound [I] of the present invention is 0 or 1, and is preferably 0.

q in the compound [I] of the present invention is 0, 1 or 2, and when q is 2, each $R_3$ independently represents the same or different substituent. Preferably q is 1 or 2, and more preferably q is 1.

----- in the compound [I] of the present invention is single or double bond, and is preferably single bond.

In the compound [I] of the present invention, the options and preferred embodiments for the above substituents as presented include all combinations of these forms as long as they are consistent combinations.

Preferred embodiments of the compound [I] of the present invention are given below.

(1) Those in which the ring A in Formula [I] is phenyl, and L is —O—.
(2) Those in which $R_2$ in Formula [I] is —O-lower alkyl.
(3) Those in which $R_3$ in Formula [I] is halogen, lower alkynyl, lower alkyl or —S-lower alkyl optionally substituted with halogen.

More preferred embodiments of the compound [I] are given below.

(1) Those in which the ring A in Formula [I] is phenyl, L is —O— and n is 0.
(2) Those in which $R_2$ in Formula [I] is methoxy.
(3) Those in which $R_3$ in Formula [I] is halogen or lower alkyl.

Still more preferred embodiments of the compound [I] are given below.

(1) Those in which L in Formula [I] is —O—, m and n are each 0, and

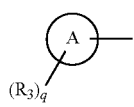
is phenyl, fluorophenyl, difluorophenyl, chlorophenyl, bromophenyl, ethynylphenyl, methylphenyl, trifluoromethylthio or methyl- and fluorine-substituted phenyl.
In the present invention, moreover, a compound selected from the group consisting of the following compounds or their salts is preferred.
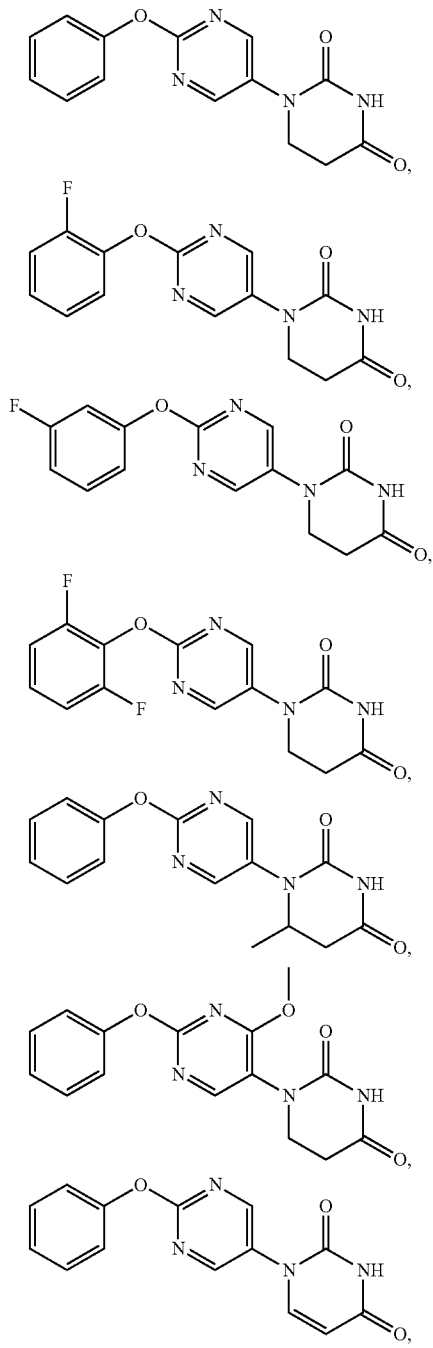
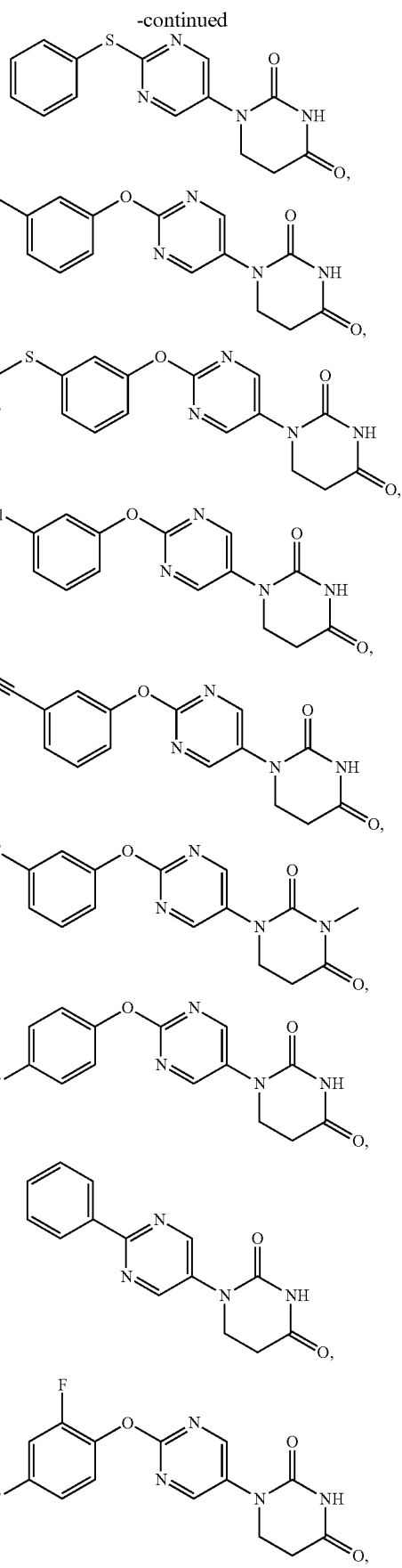

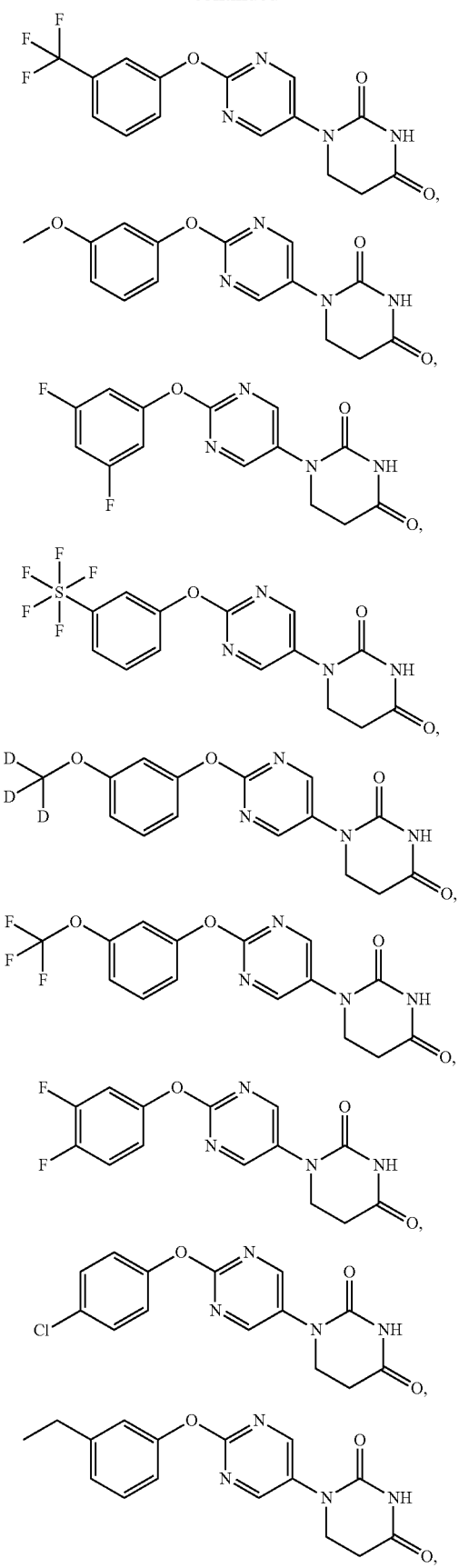
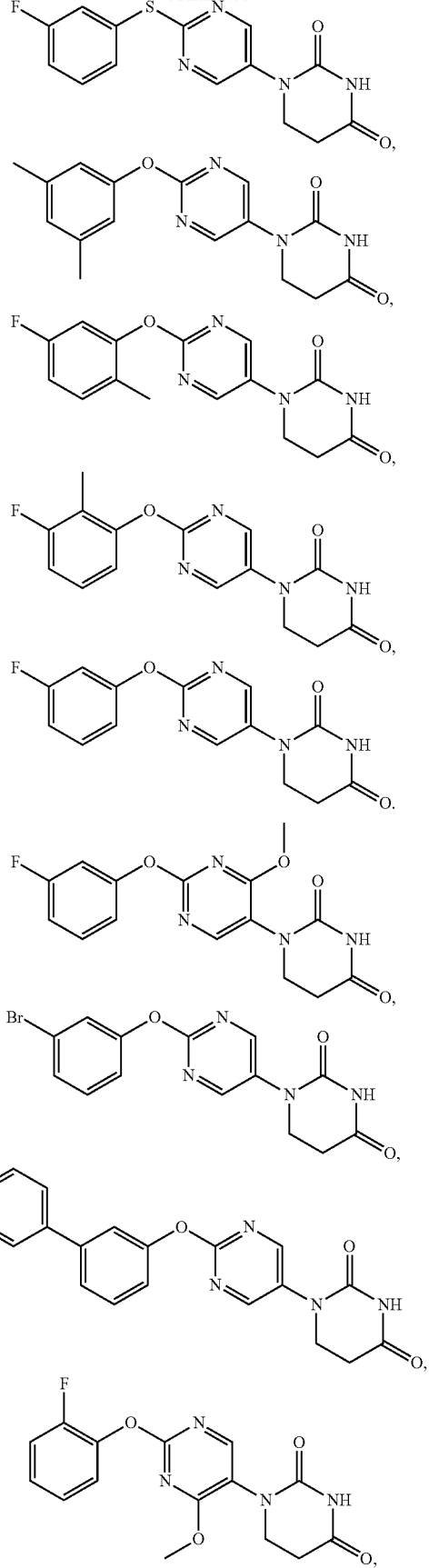

-continued

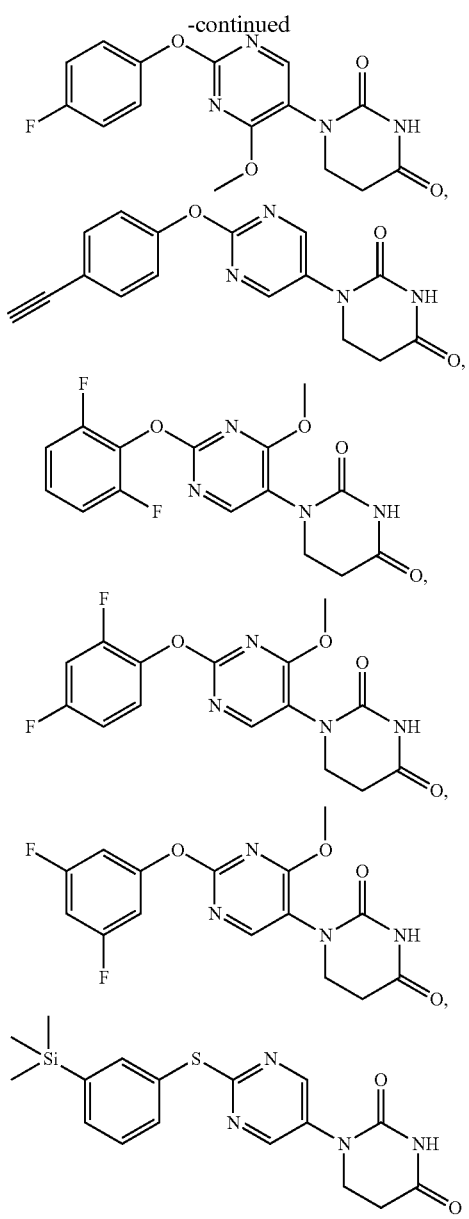

In this specification, the options and preferred embodiments for the different features of the compound, method and composition of the present invention as presented include all possible combinations of the options and preferred embodiments for these different features as long as they are consistent combinations.

Methods for manufacturing the compound [I] of the present invention are explained below. The compound [I] of the present invention can be manufactured based on the manufacturing methods described below for example. The manufacturing methods described below are examples, and the method for manufacturing the compound [I] is not limited thereby.

In the reaction formulae below, when performing an alkylation reaction, hydrolysis reaction, amination reaction, esterification reaction, amidation reaction etherification reaction, nucleophilic substitution reaction, addition reaction, oxidation reaction, reduction reaction or the like, these reactions are themselves performed by known methods.

Examples of such methods include the methods described in Experimental Chemistry (Fifth Edition, edited by The Chemical Society of Japan, Maruzen Co., Ltd.); Organic Functional Group Preparations Second Edition, Academic Press, Inc., 1989; Comprehensive Organic Transformations, VCH Publishers, Inc., 1989; and P. G. M. Wuts and T. W. Greene, Greene's Protective Groups in Organic Synthesis (Fourth Edition, 2006) and the like.

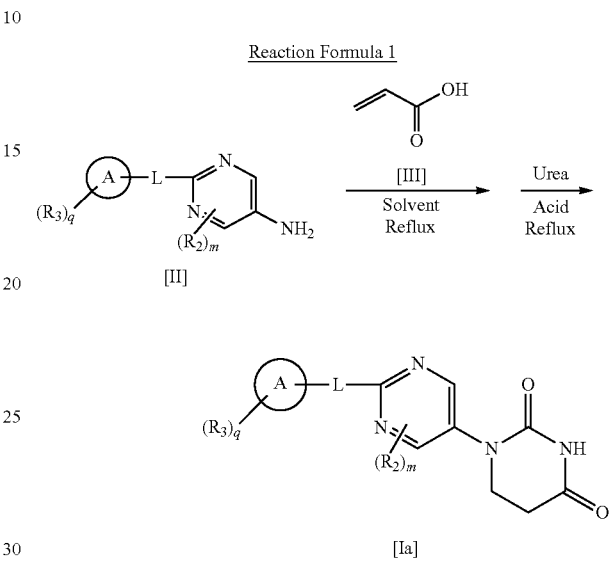

Reaction Formula 1

(In the formula, all symbols are as defined above.)

A compound [Ia] included in the compound [I] of the present invention can be manufactured by the reaction shown by the Reaction Formula 1 above. Specifically, a compound [III](acrylic acid) is added by 1,4-addition to the amino group of the compound [II], and the amino group of the product is then converted with urea to a urea derivative, which can then be cyclized (intramolecular amidation) to manufacture the compound [Ia].

The "solvent" used in this reaction may be any solvent that is inactive in the reaction, and examples thereof include water, ethers (such as dioxane, tetrahydrofuran, diethyl ether, 1,2-dimethoxyethane, diethylene glycol dimethyl ether or ethylene glycol dimethyl ether), halohydrocarbons (such as methylene chloride, chloroform, 1,2-dichloroethane or carbon tetrachloride), aromatic hydrocarbons (such as benzene, toluene or xylene), lower alcohols (such as methanol, ethanol or isopropanol) and polar solvents (such as N,N-dimethylformamide (DMF), N-methylpyrrolidine (NMP), dimethyl sulfoxide (DMSO), hexamethylphosphoric acid triamide or acetonitrile). One of these solvents alone or a mixture of two or more kinds may be used.

The "acid" used in this reaction may be an inorganic acid, organic acid or the like for example. Examples of the "inorganic acid" include hydrochloric acid, sulfuric acid, nitric acid, hydrobromic acid and phosphoric acid. Examples of the "organic acid" include acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid.

The other reaction conditions (reaction temperature, reaction time, etc.) may be selected appropriately based on known 1,4-addition reactions and amidation reactions.

Reaction Formula 2

[Reaction scheme showing compound [IV] with A ring bearing (R3)q and L1H, plus compound [V] with X-substituted pyrimidine bearing (R2)m linked to uracil bearing (R1)n, reacting with Base/Solvent to give compound [Ib]]

(In the formula, X is a leaving group, L₁ is —O—, —S— or lower alkylene, and the other symbols are as defined above.)

A compound [Ib] included in the compound [I] of the present invention can be manufactured by the reaction represented by the Reaction Formula 2. Specifically, the leaving group X of compound [V] is dissociated, and replaced with the compound [IV] to manufacture the compound [Ib].

Examples of the "leaving group" used in the reaction above include halogen, $C_{1-18}$ alkanesulfonyl, lower alkanesulfonyloxy, arenesulfonyloxy, aralkylsulfonyloxy, perhalomethanesulfonyloxy, sulfonio, toluenesulfoxy and the like. Examples of preferred leaving group in the reaction include halogen.

Examples of "halogen" above include fluorine, chlorine, bromine and iodine.

Examples of the "$C_{1-18}$ alkanesulfonyl" include $C_{1-18}$ linear or branched alkanesulfonyl, and specific examples include methanesulfonyl, 1-propanesulfonyl, 2-propanesulfonyl, butanesulfonyl, cyclohexanesulfonyl, dodecanesulfonyl, octadecanesulfonyl and the like.

Examples of the "lower alkanesulfonyloxy" include $C_{1-6}$ linear or branched alkanesulfonyloxy, and specific examples include methanesulfonyloxy, ethanesulfonyloxy, 1-propanesulfonyloxy, 2-propanesulfonyloxy, 1-butanesulfonyloxy, 3-butanesulfonyloxy, 1-pentanesulfonyloxy, 1-hexanesulfonyloxy and the like.

Examples of the "arenesulfonyloxy" include naphthalenesulfonyloxy and benzenesulfonyloxy, which may have 1 to 3 substituents selected from the group consisting of halogen, nitro, $C_{1-6}$ linear or branched alkoxy and $C_{1-6}$ linear or branched alkyl groups on the phenyl ring. Specific examples of these "benzenesulfonyloxy which may have substituents" include benzenesulfonyloxy, 4-methylbenzenesulfonyloxy, 2-methylbenzenesulfonyloxy, 4-nitrobenzenesulfonyloxy, 4-methoxybenzenesulfonyloxy, 2-nitrobenzenesulfonyloxy, 3-chlorobenzenesulfonyloxy and the like. Specific examples of "naphthalenesulfonyloxy" include α-naphthalenesulfonyloxy, β-naphthalenesulfonyloxy and the like.

Examples of the "aralkanesulfonyloxy" include naphthyl-substituted $C_{1-6}$ linear or branched alkanesulfonyloxy and phenyl-substituted $C_{1-6}$ linear or branched alkanesulfonyloxy which may have 1 to 3 substituents selected from the group consisting of halogen, nitro, $C_{1-6}$ linear or branched alkoxy and $C_{1-6}$ linear or branched alkyl on the phenyl ring. Specific examples of these "phenyl-substituted alkanesulfonyloxy" include phenylmethanesulfonyloxy, 2-phenylethanesulfonyloxy, 4-phenylbutanesulfonyloxy, 4-tolylmethanesulfonyloxy, 2-tolylmethanesulfonyloxy, (4-nitrophenyl)methanesulfonyloxy, (4-methoxyphenyl)methanesulfonyloxy, (3-chlorophenyl)methanesulfonyloxy and the like. Examples of "naphthyl-substituted alkanesulfonyloxy" include α-naphthylmethanesulfonyloxy, β-naphthylmethanesulfonyloxy and the like.

A specific example of "perhaloalkanesulfonyloxy" group is trifluoromethanesulfonyloxy.

Specific examples of the "sulfonio" include dimethylsulfonio, diethylsulfonio, dipropylsulfonio, di(2-cyanoethyl)sulfonio, di(2-nitroethyl)sulfonio, di-(aminoethyl)sulfonio, di(2-methylaminoethyl)sulfonio, di-(2-dimethylaminoethyl)sulfonio, di-(2-hydroxyethyl)sulfonio, di-(3-hydroxypropyl)sulfonio, di-(2-methoxyethyl)sulfonio, di-(2-carbamoylethyl)sulfonio, di-(2-carboxyethyl)sulfonio, di-(2-methoxycarbonylethyl)sulfonio, diphenylsulfonio and the like.

The "solvent" used in this reaction may be any solvent that is inactive in the reaction, and examples thereof include water, ethers (such as dioxane, tetrahydrofuran, diethyl ether, 1,2-dimethoxyethane, diethylene glycol dimethyl ether and ethylene glycol dimethyl ether), halohydrocarbons (such as methylene chloride, chloroform, 1,2-dichloroethane and carbon tetrachloride), aromatic hydrocarbons (such as benzene, toluene and xylene), lower alcohols (such as methanol, ethanol and isopropanol) and polar solvents (such as N,N-dimethylformamide (DMF), N-methylpyrrolidine (NMP), dimethyl sulfoxide (DMSO), hexamethylphosphoric acid triamide and acetonitrile). One of these solvents alone or a mixture of two or more kinds may be used.

The "base" used in this reaction may be an inorganic base, organic base or the like for example. Examples of the "inorganic base" include alkali metal hydroxides (such as sodium hydroxide and potassium hydroxide), alkali earth metal hydroxides (such as magnesium hydroxide and calcium hydroxide), alkali metal carbonates (such as sodium carbonate and potassium carbonate), alkali earth metal carbonates (such as magnesium carbonate and calcium carbonate), alkali metal bicarbonate salts (such as sodium bicarbonate and potassium bicarbonate) and the like. Examples of the "organic base" include trialkylamines (such as trimethylamine and triethylamine), picoline, and 1,5-diazabicyclo[4.3.0]non-5-ene, 1,4-diazabicyclo[2.2.2]octane, 1,8-diazabicyclo[5.4.0]undec-7-ene and the like.

The other reaction conditions (reaction temperature, reaction time, etc.) may be determined appropriately based on known nucleophilic reactions.

In each of the reactions in the above reaction formulae, the reaction product can be used in the next reaction either as is in the form of the reaction solution or as a crude product, but it can also be isolated from the reaction mixture by normal methods and easily purified by normal separation techniques. Examples of normal separation techniques include recrystallization, distillation and chromatography.

The starting raw material compounds, intermediate compounds and object compounds in each of the above steps and the compound [I] of the present invention itself all include geometric isomers, stereoisomers, optical isomers and tautomers. The respective isomers can be separated by ordinary optical resolution methods. They can also be manufactured from raw material compounds having suitable optical activity.

The compound [I] of the present invention can be manufactured by the synthesis methods shown in the reaction formulae above, or by analogous methods.

Unless specific production methods are specified, the raw material compounds used in the manufacture of the compound [I] of the present invention may be commercial compounds, or may be produced by known methods or analogous methods.

The starting raw material compounds and object compounds in each step above may be used in the form of appropriate salts. Examples of such salts include salts similar to those given as examples of salts of compound [I] of the present invention below.

When the compounds obtained in each step or commercial products are free compounds, they can be converted to the object salts by known methods. When the compounds obtained in each step or commercial products are salts, they can be converted to free form or into other object salts by known methods.

The compound [I] of the present invention also includes embodiments that are pharmaceutically acceptable salts, and in some cases the compounds may also form an acid addition salt or a salt with a base depending on the kinds of substituents. Examples of the "acid" here include inorganic acids such as hydrochloric acid, hydrobromic acid, nitric acid, sulfuric acid and phosphoric acid; and organic acids such as methanesulfonic acid, p-toluenesulfonic acid, acetic acid, citric acid, tartaric acid, maleic acid, fumaric acid, malic acid, lactic acid and the like. Examples of the "base" include inorganic bases such as sodium hydroxide, potassium hydroxide, calcium hydroxide, sodium carbonate, potassium carbonate, sodium bicarbonate and potassium bicarbonate; organic bases such as methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline and choline; and ammonium salts and the like. The compound may also form a salt with an amino acid such as lysine, arginine, aspartic acid, glutamic acid or the like.

The present invention also encompasses various hydrates, solvates and crystal polymorphisms of the compound [I] and salts thereof.

The compound [I] of the present invention also includes compounds in which one or more isotope atoms have been substituted for one or more atoms. Examples of isotope atoms include deuterium ($^2$H), tritium ($^3$H), $^{13}$C, $^{15}$N, $^{18}$O and the like.

The compound [I] of the present invention includes pharmaceutically acceptable prodrugs. Examples of substituents that can be modified to make prodrugs include reactive functional groups such as —OH, —COOH, amino and the like. The modifying groups of these functional groups are selected appropriately from the "substituents" in this specification.

The compound [I] or a salt thereof of the present invention may be in the form of a pharmaceutically acceptable co-crystal or co-crystal salts. A co-crystal or co-crystal salt here means a crystalline substance composed at room temperature of two or more independent solids each having different physical properties (such as structure, melting point, heat of fusion and the like). Co-crystals and co-crystal salts can be manufactured appropriately by well-known co-crystallization methods.

The compound [I] and a salt thereof of the present invention have excellent effects in the treatment, prevention and/or diagnosis of seizure in disease involving epileptic seizure or convulsive seizure. The term epileptic seizure is applicable to any of the seizure types classified below: focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizures of unknown onset including motor seizure (including tonic-clonic seizure and epileptic spasms) and non-motor seizure (including behavior arrest seizure).

Examples of the disease involving epileptic seizure or convulsive seizure include Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.).

The compound [I] or a salt thereof of the present invention is also effective in the treatment, prevention and/or diagnosis of multiple drug resistant seizure, refractory seizure, acute symptomatic seizure, febrile seizure and status epilepticus. In the present invention, multiple drug resistant seizure and refractory seizure are defined as seizure that cannot be controlled because one or two or more antiepileptic drugs are ineffective or insufficiently effective or the like, regardless of the type of epileptic seizure as described above.

Moreover, the compound [I] and a salt thereof of the present invention have excellent features for use as active ingredients in pharmaceuticals, and for example have excellent features such as few side effects, tolerability, stability (storage stability, metabolic stability, etc.) and the like. These groups of compounds of the present invention also have effects as preventative and/or therapeutic agents against refractory epileptic seizure in which conventional drug therapy is not successful.

Next, a medical preparation (hereunder also called a "pharmaceutical composition") containing a compound [I] or a salt thereof of the present invention as an active ingredient is explained.

The medical preparation is obtained by formulating a compound [I] or a salt thereof of the present invention in the form of an ordinary medical preparation, and is prepared using a compound [I] or a salt thereof of the present invention and a pharmaceutically acceptable carrier. Examples of the carrier include commonly used diluents or excipients such as fillers, bulking agents, binders, humectants, disintegrants, surfactants, lubricants and the like.

Such a medical preparation can be selected from various forms according to the therapeutic objective, and examples thereof include tablets, pills, powders, liquids, suspensions, emulsions, granules, capsules, suppositories, injections (liquids, suspensions, etc.) and the like.

A wide range of known carriers may be used when molding the preparation in the form of a tablet, and examples thereof include excipients such as lactose; binders such as polyvinylpyrrolidone; disintegrants such as starch; absorption aids such as sodium lauryl sulfate; humectants such as glycerin and starch; adsorbants such as colloidal silicic acid; and lubricants such as magnesium stearate, polyethylene glycol and the like.

Moreover, the tablet may as necessary be made into a tablet with an ordinary coating, such as for example a sugar-coated tablet, gelatin-coated tablet, enteric coated tablet, film-coated tablet, double tablet or multilayer tablet.

A wide range of known carriers may be used when molding the preparation in the form of a pill, and examples thereof include excipients such as glucose; binders such as gum arabic powder; and disintegrants such as laminaran and the like.

A wide range of known diluents may be used when forming the preparation as a liquid, emulsion or suspension, and examples thereof include water and the like. Ordinary solubilizing agents and buffers may also be included, as well as colorants, preservatives, aromatics, flavorings, sweeteners and other drugs and the like as necessary.

A wide range of known carriers may be used when forming the preparation as a suppository, and examples thereof include cocoa butter and the like.

When the preparation is an injection, the liquid, emulsion or suspension is preferably sterilized, and is also preferably isotonic with blood. An amount of sodium chloride sufficient to prepare an isotonic injection may be included in the injection, and another drug, soothing agent or the like may also be included.

The amount of the compound [I] or a salt thereof that is contained in the medical preparation is not particularly limited and may be selected appropriately from a wide range, but normally the compound [I] or a salt thereof of the present invention is preferably contained in the amount of 1% to 70% of the medical preparation.

The method for administering the medical preparation of the present invention is not particularly limited, and it can be administered by a method suited to the dosage form, the age and sex of the patient, the disease status and other conditions. For example, it can be administered orally if it is in the form of a tablet, pill, liquid, suspension, emulsion, granules or capsules. If it is an injection, it can be administered intravenously either alone or in a mixture with an ordinary replacement fluid such as glucose or amino acids, or else it can be administered by itself intramuscularly, intradermally, subcutaneously or intraperitoneally as necessary. In the case of a suppository, it can be administered in the rectum.

The dose of the medical preparation may be selected according to the administration method, the age and sex of the patient, the severity of the disease and other conditions, but normally 0.01 to 100 mg or preferably 0.1 to 50 mg per 1 kg of body weight can be administered per day in one or more administrations.

This dose is affected by various conditions, and in some cases a dose below the aforementioned range may be sufficient, while in others a dose above the aforementioned range may be necessary.

The compound [I] or a salt thereof of the present invention can be used in combination with various treatment or preventative agents for disease for which the compound [I] is thought to be effective. Such combined use may be by simultaneous administration, or else by separate administration, either continuously or with a suitable interval in between. Preparations that are administered simultaneously may be formulated separately or combination.

A pharmaceutical composition containing the compound [I] or a salt thereof of the present invention together with a pharmaceutically acceptable carrier and/or excipient is provided by one embodiment of the present invention.

Another embodiment provides a therapeutic, preventative and/or diagnostic agent for seizure in disease involving epileptic seizure or convulsive seizure (including multiple drug resistant seizure, refractory seizure, acute symptomatic seizure, febrile seizure and status epilepticus), containing the compound [I] or a salt thereof of the present invention together with a pharmaceutically acceptable carrier and/or excipient.

Yet another embodiment provides a therapeutic, preventative and/or diagnostic pharmaceutical composition for seizure in disease involving epileptic seizure or convulsive seizure (including multiple drug resistant seizure, refractory seizure, acute symptomatic seizure, febrile seizure and status epilepticus), containing the compound [I] or a salt thereof of the present invention together with a pharmaceutically acceptable carrier and/or excipient.

Yet another embodiment provides a method for treating, preventing and/or diagnosing seizure in disease involving epileptic seizure or convulsive seizure (including multiple drug resistant seizure, refractory seizure, acute symptomatic seizure, febrile seizure and status epilepticus), which comprises administering to a human in need thereof an effective amount of the compound [I] or a salt thereof of the present invention.

Yet another embodiment provides the compound [I] or a salt thereof of the present invention for use in the treatment, prevention and/or diagnosis of seizure in disease involving epileptic seizure or convulsive seizure (including multiple drug resistant seizure, refractory seizure, acute symptomatic seizure, febrile seizure and status epilepticus).

Yet another embodiment provides the use of the compound [I]or a salt thereof of the present invention in the manufacture of a drug for treating, preventing and/or diagnosing seizure in disease involving epileptic seizure or convulsive seizure (including multiple drug resistant seizure, refractory seizure, acute symptomatic seizure, febrile seizure and status epilepticus).

EXAMPLES

The present invention is explained in further detail below through the following Test Examples, Reference Examples and Examples, but these do not limit the present invention, and these may be changed to the extent that they do not deviate from the scope of the present invention.

The following abbreviations are used in this Description.
REX: Reference Example number
EX: Example number
STR: Structural formula (in the formula, the label "Chiral" indicates the absolute configuration of a structure)

RProp: Manufacturing method (numbers indicate that the compound was manufactured using the corresponding raw materials in the same way as the reference example compound having that number as a reference example number)

Prop: Manufacturing method (numbers indicate that the compound was manufactured using the corresponding raw materials in the same way as the example compound having that number as an example number)

Data: Physical property data (NMR1: δ (ppm) in $^1$H-NMR in dimethylsulfoxide-$d_6$; NMR2: δ (ppm) in $^1$H-NMR in $CDCl_3$)

Ph: Phenyl
9-BBN: 9-Borabicyclo[3.3.1]nonane
CDI: 1,1'-Carbonyldiimidazole
DBU: 1,8-Diazabicyclo[5.4.0]-7-undecene
DIBOC: Di-t-butyl dicarbonate
WSC: 3-Ethyl-1-(3-dimethylaminopropyl)carbodiimide
DEAD: Diethylazodicarboxylate
DPPA: Diphenylphosphoryl azide
HOBt: 1-Hydroxybenzotriazole
NCS: N-Chlorosuccinimide
DCC: Dicyclohexylcarbodiimide
DHP: 3,4-Dihydro-2H-pyran
DMAP: 4-(Dimethylamino)pyridine
ZC1: Benzyl chloroformate
PPTS: Pyridinium p-toluenesulfonate
MCPBA: m-Chloroperbenzoic acid
$BBr_3$: Boron tribromide
n-BuLi: n-Butyl lithium
NaH: Sodium hydride
DIPEA: Diisopropylethylamine
KOtBu: Potassium t-butoxide
LDA: Lithium diisopropylamide
LHMDS: Lithium hexamethyldisilazide
NaOtBu: Sodium t-butoxide
DIBAL: Diisobutyl aluminum hydride
LAH: Lithium aluminum hydride
$NaBH_4$: Sodium borohydride
Pd/C: Palladium on carbon
AcOEt: Ethyl acetate
DCE: 1,2-Dichloroethane
DCM: Dichloromethane
DMA: N,N-Dimethylacetamide
DME: Dimethoxyethane
DMF: N,N-Dimethylformamide
DMSO: Dimethylsulfoxide
$Et_2O$: Diethyl ether
MeOH: Methanol
EtOH: Ethanol
Hexane: n-Hexane
IPA: 2-Propanol
IPE: Diisopropyl ether
MeCN: Acetonitrile
MEK: 2-Butanone
NMP: N-Methylpyrrolidone
PEG: Polyethylene glycol
TEA: Triethylamine
TFA: Trifluoracetic acid
THF: Tetrahydrofuran
AcOH: Acetic acid
HCl: Hydrochloric acid
KOH: Potassium hydroxide
LiOH: Lithium hydroxide
NaOH: Sodium hydroxide
$K_3PO_4$: Tripotassium phosphate
$Cs_2CO_3$: Cesium carbonate
$K_2CO_3$: Potassium carbonate
$KHCO_3$: Potassium bicarbonate
$NaHCO_3$: Sodium bicarbonate
AcONa: Sodium acetate In the examples below, "room temperature" normally indicates from about 10° C. to about 35° C. The ratios indicated for mixed solvents are volume ratios unless otherwise specified. Percentages indicate weight % unless otherwise specified.

The $^1$H-NMR (proton nuclear magnetic resonance) spectra were measured by Fourier transform type NMR (using any of Bruker AVANCE 300 (300 MHz), Bruker AVANCE 500 (500 MHz), Bruker AVANCE III 400 (400 MHz) or Bruker AVANCE III 500 (500 MHz).

When a basic gel is described for silica gel column chromatography, an aminopropylsilane bonded silica gel is used.

The absolute configuration of the compound was determined by known X-ray crystal structure analysis methods (for example, Shigeru Oba and Shigenobu Yano, "Basic Course for Chemists 12, X-ray Crystal Structure Analysis" (First Edition, 1999)), or estimated from empirical rules of Shi asymmetric epoxidation (Waldemar Adam, Rainer T. Fell, Chantu R. Saha-Moller and Cong-Gui Zhao:Tetrahedron: Asymmetry 1998, 9, 397-401. Yuanming Zhu, Yong Tu, Hongwu Yu, Yian Shi:Tetrahedron Lett. 1988, 29, 2437-2440).

REFERENCE EXAMPLES

Reference Example 1

5-Nitro-2-phenoxypyrimidine

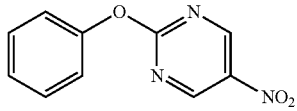 [SMILES: O=[N+]([O-])c1cnc(Oc2ccccc2)nc1]

Phenol (6.61 mL) and $K_2CO_3$ (12.99 g) were suspended in DMF (80 mL), 2-chloro-5-nitropyrimidine (10 g) was added, and the mixture was stirred overnight at room temperature. Water was added to the reaction solution, and the resulting solid was washed with water to obtain the object compound (6.55 g).

NMR2: 7.17-7.24 (2H, m), 7.31-7.39 (1H, m), 7.45-7.53 (2H, m), 9.33 (2H, s).

Reference Example 2

2-Phenoxypyrimidine-5-amine

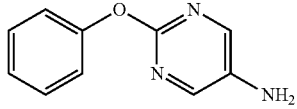 [SMILES: Nc1cnc(Oc2ccccc2)nc1]

5-Nitro-2-phenoxypyrimidine (7.45 g) and 50% aqueous 10% Pd/C (3 g) were suspended in EtOH (100 mL), and stirred for 16 hours at room temperature under a hydrogen atmosphere. The reaction solution was filtered through Celite, the filtrate was concentrated, and the resulting solid was washed with IPE to obtain the object compound (4.73 g).

NMR2: 3.50 (2H, brs), 7.13-7.24 (3H, m), 7.35-7.45 (2H, m), 8.07 (2H, s).

Reference Example 3

2-(2-Fluorophenoxy)-5-nitropyrimidine

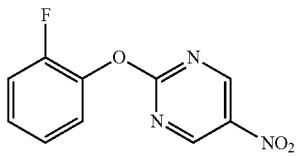

o-Fluorophenol (6.71 mL) and K$_2$CO$_3$ (12.99 g) were suspended in DMF (100 mL), after which 2-chloro-5-nitropyrimidine (10 g) was added and stirred for 8 hours at room temperature. Water was added to the reaction solution, and the resulting solid was washed with water to obtain the object compound (13.67 g).

NMR2: 7.20-7.38 (4H, m), 9.33 (2H, s).

Reference Example 4

2-(2-Fluorophenoxy)pyrimidine-5-amine

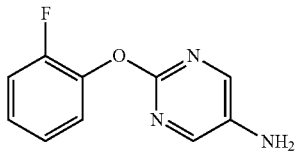 [SMILES: Nc1cnc(Oc2ccccc2F)nc1]

2-(2-Fluorophenoxy)-5-nitropyrimidine (13.67 g) and 50% aqueous 10% Pd/C (3 g) were suspended in EtOH (130 mL), and stirred for 1 hour at room temperature under a hydrogen atmosphere. The reaction solution was filtered through Celite, the filtrate was concentrated, and the resulting solid was washed with IPE to obtain the object compound (8.25 g).

NMR2: 3.51 (2H, brs), 7.13-7.30 (4H, m), 8.05 (2H, s).

Reference Example 5

2-(3-Fluorophenoxy)-5-nitropyrimidine

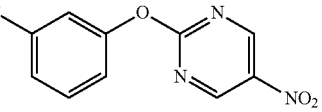

m-Fluorophenol (5.45 mL) and K$_2$CO$_3$ (10.40 g) were suspended in DMF (80 mL), 2-chloro-5-nitropyrimidine (8 g) was added, and the mixture was stirred overnight at room temperature. Water was added to the residue, which was then extracted with AcOEt, and the organic layer was separated, washed with water and saturated saline, dried with sodium sulfate, and concentrated to obtain the object compound (8.63 g).

NMR2: 6.93-7.12 (3H, m), 7.38-7.48 (1H, m), 9.34 (2H, s).

Reference Example 6

2-(3-Fluorophenoxy)pyrimidine-5-amine

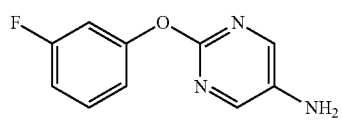 [SMILES: Nc1cnc(Oc2cccc(F)c2)nc1]

2-(3-Fluorophenoxy)-5-nitropyrimidine (8.65 g) and 50% aqueous 10% Pd/C (3 g) were suspended in EtOH (100 mL), and stirred for 16 hours at room temperature under a hydrogen atmosphere. The reaction solution was filtered through Celite, and the filtrate was concentrated to obtain a crude product. The crude product was purified by medium pressure preparative liquid chromatography (DMC/AcOEt=10:1→1:1), and the resulting solid was then washed with hexane to obtain the object compound (3.77 g).

NMR2: 3.55 (2H, brs), 6.86-7.00 (3H, m), 7.30-7.39 (1H, m), 8.08 (2H, s).

Reference Example 7

1-[2-(Methylthio)pyrimidin-5-yl]pyrimidine-2,4(1H,3H)-dione

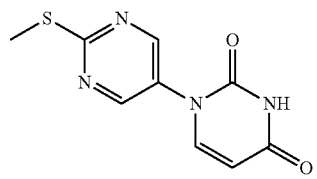 [SMILES: CSc1ncc(-n2ccc(=O)[nH]c2=O)cn1]

A mixture of 5-bromo-2-(methylthio)pyrimidine (2.77 g), uracil (2.27 g), copper iodide (0.257 g), picolinic acid (0.33 g) and K$_3$PO$_4$ (5.73 g) was suspended in DMSO (30 mL), and stirred overnight at 150° C. under a nitrogen atmosphere. Aqueous citric acid solution was added to the reaction solution, which was then extracted with AcOEt. The organic layer was separated, washed with water and saturated saline, dried with sodium sulfate and concentrated to obtain a crude product. The crude product was purified by medium pressure preparative liquid chromatography (Hexane:AcOEt=10:1→0:1) to obtain the object compound (577 mg).

NMR1: 2.56 (3H, s), 5.77 (1H, d, J=7.9 Hz), 7.80 (1H, d, J=7.9 Hz), 8.76 (2H, s), 11.62 (1H, brs).

Reference Example 8

2-(Dodecylthio)-5-nitropyrimidine

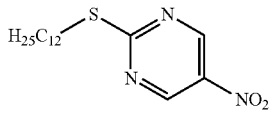

Dodecylmercaptan (24.77 mL) was dissolved in DMF (150 mL) and cooled to 0° C., 60% NaH (4.14 g) was added and stirred for 10 minutes, and 2-chloro-5-nitropyrimidine (15 g) was added to the mixture, which was then stirred for 1 hour at 0° C. Water was added to the reaction solution, and the resulting solid was washed with water to obtain the object compound (26.01 g).

NMR2: 0.88 (3H, t, J=7.0 Hz), 1.18-1.38 (16H, m), 1.38-1.50 (2H, m), 1.64-1.76 (2H, m), 3.23 (2H, t, =7.5 Hz), 9.23 (2H, s).

Reference Example 9

2-(Dodecylthio)pyrimidine-5-amine

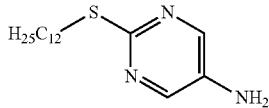

2-(Dodecylthio)-5-nitropyrimidine (26.01 g) was dissolved in EtOH (250 mL), ammonium chloride (25.6 g) aqueous solution (100 mL) and zinc powder (52.2 g) were added, and the mixture was stirred under reflux for 5 hours. AcOEt was added to the reaction solution and stirred overnight, after which the reaction solution was filtered through Celite, and the filtrate was concentrated. Water was added to the residue, which was then extracted with AcOEt. The organic layer was separated, washed with water and saturated saline, dried with sodium sulfate, and concentrated to obtain a crude product. The crude product was purified by medium pressure preparative liquid chromatography (Hexane:AcOEt=4:1→1:1), and washed with hexane to obtain the object compound (20.17 g).

NMR2: 0.88 (3H, t, J=7.0 Hz), 1.15-1.40 (16H, m), 1.40-1.51 (2H, m), 1.62-1.81 (2H, m), 3.10 (2H, t, J=7.4 Hz), 3.49 (2H, brs), 8.08 (2H, s).

Reference Example 10

1-[2-(Dodecylthio)pyrimidin-5-yl]-5,6-dihydropyrimidine-2,4(1H,3H)-dione

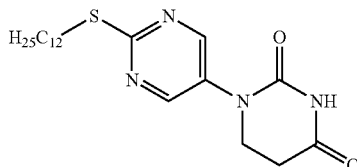

2-(Dodecylthio)pyrimidine-5-amine (11 g) was dissolved in toluene (100 mL), acrylic acid (3.83 mL) was added, and the mixture was stirred overnight at 110° C. The reaction solution was concentrated, the residue was dissolved in AcOH (100 mL), urea (3.35 g) was added, and the mixture was stirred for 2 days at 110° C. The reaction solution was concentrated and washed with saturated sodium bicarbonate aqueous solution, and the resulting crystal was filtered out. The resulting solid was dissolved in a 10% MeOH/DCM mixed solution, dried with sodium sulfate and filtered, and the filtrate was concentrated. The resulting solid was washed with EtOH to obtain the object compound (5.67 g).

NMR2: 0.88 (3H, t, J=7.0 Hz), 1.17-1.38 (16H, m), 1.38-1.50 (2H, m), 1.68-1.79 (2H, m), 2.89 (2H, t, J=6.7 Hz), 3.14 (2H, t, J=7.4 Hz), 3.88 (2H, t, J=6.7 Hz), 7.48 (1H, brs), 8.52 (2H, s).

Reference Example 11

1-[2-(Dodecylsulfonyl)pyrimidin-5-yl]-5,6-dihydropyrimidine-2,4(1H,3H)-dione

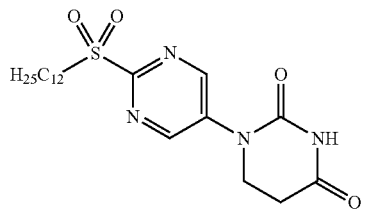

1-[2-(Dodecylthio)pyrimidin-5-yl]-5,6-dihydropyrimidine-2,4(1H,3H)-dione (7.17 g) was suspended in DCM (80 mL) and cooled, after which aqueous 77% MCPBA (10.23 g) was added, and the mixture was stirred overnight at room temperature. Dimethylsulfide was added to the reaction solution and stirred, after which saturated sodium bicarbonate aqueous solution was added and the DCM was distilled off under reduced pressure. The resulting solid was washed with water to obtain the object compound (7.15 g).

NMR1: 0.85 (3H, t, J=7.1 Hz), 1.15-1.45 (18H, m), 1.60-1.73 (2H, m), 2.78 (2H, t, J=6.6 Hz), 3.53-3.61 (2H, m), 4.01 (2H, t, J=6.6 Hz), 9.08 (2H, s), 10.83 (1H, brs).

Reference Example 12

1-[2-(Methylthio)pyrimidin-5-yl]-5,6-dihydropyrimidine-2,4(1H,3H)-dione

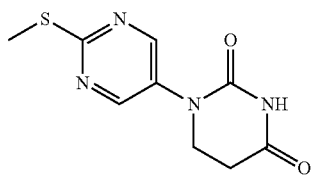 [SMILES: CSc1ncc(N2CCC(=O)NC2=O)cn1]

2-(Methylthio)pyrimidine-5-amine (4.61 g) was suspended in water (25 mL), acrylic acid (4.48 mL) was added, and the mixture was stirred for 2 days at 70° C. in a nitrogen atmosphere. The reaction solution was concentrated, the residue was dissolved in AcOH (25 mL), urea (2.94 g) was added, and the mixture was stirred for 3 days at 90° C. The reaction solution was concentrated, and the residue was neutralized by addition of saturated sodium bicarbonate aqueous solution and extracted with AcOEt. The organic layer was separated, washed with water and saturated saline, dried with sodium sulfate, and concentrated to obtain a crude product. The crude product was purified by medium pressure preparative liquid chromatography (Hexane:AcOEt=4:1→0:1), and washed with EtOH to obtain the object compound (478 mg).

NMR2: 2.58 (3H, s), 2.90 (2H, t, J=6.7 Hz), 3.89 (2H, t, J=6.7 Hz), 7.61 (1H, brs), 8.54 (2H, s).

Reference Example 13

1-[2-(Methylsulfonyl)pyrimidin-5-yl]-5,6-dihydro-pyrimidine-2,4(1H,3H)-dione

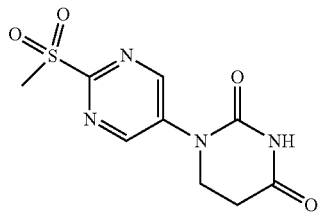 [SMILES: CS(=O)(=O)c1ncc(N2CCC(=O)NC2=O)cn1]

1-[2-(Methylthio)pyrimidin-5-yl]-5,6-dihydropyrimidine-2,4(1H,3H)-dione (520 mg) was suspended in DCM (10 mL), aqueous 77% MCPBA (1174 mg) was added, and the mixture was stirred overnight at room temperature in a nitrogen atmosphere. Dimethylsulfide was added to the reaction solution and stirred, and the solid was washed with DCM to obtain the object compound (449 mg).

NMR1: 2.78 (2H, t, J=6.6 Hz), 3.42 (3H, s), 4.01 (2H, t, J=6.6 Hz), 9.08 (2H, s), 10.82 (1H, brs).

Reference Example 14

Diethyl 2-(5-nitropyrimidin-2-yl)-2-phenylmalonate

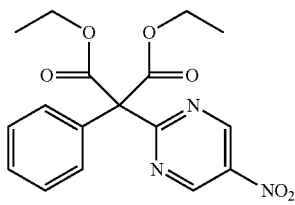 [SMILES: CCOC(=O)C(C(=O)OCC)(c1ccccc1)c1ncc([N+](=O)[O-])cn1]

Diethylphenyl malonate (21.64 mL) was suspended in DMF (100 mL) solution and ice cooled, and 60% NaH (4.02 g) was added and was stirred for 30 minutes, after which 2-chloro-5-nitropyrimidine (8.0 g) was added and stirred for 1 hour at 80° C. Water was added to the reaction solution, which was then extracted with AcOEt. The organic layer was separated, washed with water and saturated saline, dried with sodium sulfate and concentrated to obtain a crude product. The crude product was purified by medium pressure preparative liquid chromatography (Hexane:AcOEt=95:5-75:25) to obtain the object compound (10.04 g).

NMR2: 1.29 (6H, t, J=7.1 Hz), 4.37 (4H, q, J=7.1 Hz), 7.31-7.40 (3H, m), 7.43-7.50 (2H, m), 9.46 (2H, s).

Reference Example 15

2-Benzylpyrimidine-5-amine

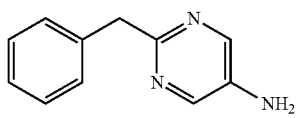 [SMILES: Nc1cnc(Cc2ccccc2)nc1]

Diethyl 2-(5-aminopyrimidin-2-yl)-2-phenylmalonate (1.13 g) was dissolved in ethylene glycol (10 mL), and 5 M NaOH aqueous solution (3.43 mL) was added and stirred for 2 days at 120° C. Citric acid aqueous solution was added to neutralize the reaction solution, which was then extracted with AcOEt. The organic layer was separated, washed with water and saturated saline, dried with sodium sulfate, and concentrated to obtain a crude product. The crude product was purified by medium pressure preparative liquid chromatography (Hexane:AcOEt=1:1→0:1) to obtain the object compound (502 mg).

NMR2: 3.59 (2H, brs), 4.18 (2H, s), 7.16-7.24 (1H, m), 7.26-7.35 (4H, m), 8.14-8.19 (2H, m).

The compounds of Reference Examples 16 to 36 were each manufactured as in Reference Examples 1 and 2.

The structural formulae and physiochemical data for the compounds of Reference Examples 16 to 36 are each shown in Tables 1-1 and 1-2.

TABLE 1-1

| REX | STR | Data |
| --- | --- | --- |
| 16 | ![structure] | NMR2; 7.38-7.45 (1H, m), 7.47-7.53 (1H, m), 7.58-7.65 (2H, m), 9.34 (2H, s). |

TABLE 1-1-continued
| REX | STR | Data |
|---|---|---|
| 17 | 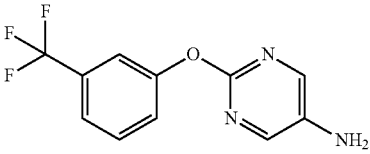 | NMR2; 3.56 (2H, brs), 7.32-7.39 (1H, m), 7.41-7.55 (3H, m), 8.07 (2H, s). |
| 18 | 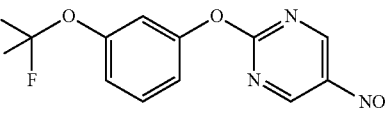 | NMR2; 7.10-7.25 (3H, m), 7.51 (1H, t, J = 8.3 Hz), 9.34 (2H, s). |
| 19 | 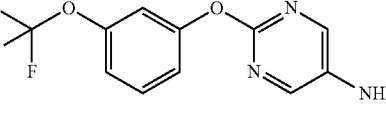 | NMR2; 3.55 (2H, brs), 7.03-7.09 (2H, m), 7.09-7.14 (1H, m), 7.40 (1H, t, J = 8.7 Hz), 8.08 (2H, s). |
| 20 | 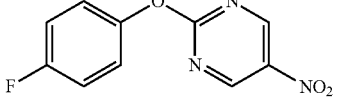 | NMR2; 7.12-7.22 (4H, m), 9.33 (2H, s). |
| 21 | 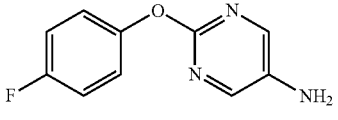 | NMR2; 3.51 (2H, brs), 7.03-7.17 (4H, m), 8.06 (2H, s). |
| 22 | 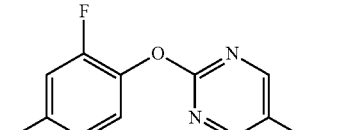 | NMR2; 6.93-7.06 (2H, m), 7.22-7.31 (1H, m), 9.33 (2H, s). |
| 23 | 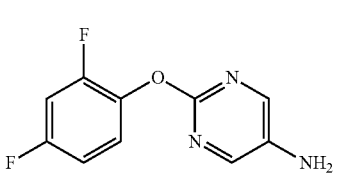 | NMR2; 3.52 (2H, brs), 6.85-6.99 (2H, m), 7.22 (1H, dt J = 5.6 Hz, 8.9 Hz), 8.04 (2H, s). |
| 24 | 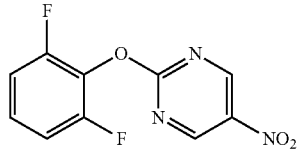 | NMR2; 7.02-7.12 (2H, m), 7.23-7.34 (1H, m), 9.35 (2H, s). |
| 25 | 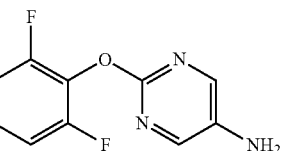 | NMR2; 3.53 (2H, brs), 6.95-7.05 (2H, m), 7.11-7.21 (1H, m), 8.04 (2H, s). |
| 26 | 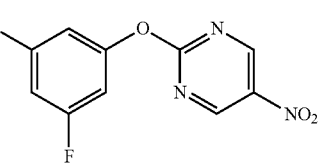 | NMR2; 6.76-6.88 (3H, m), 9.35 (2H, s). |

TABLE 1-2
| REX | STR | Data |
|---|---|---|
| 27 | 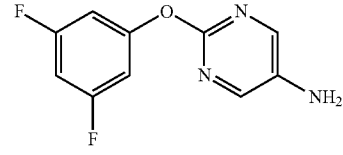 | NMR2; 3.59 (2H, brs), 6.61-6.77 (3H, m), 8.08 (2H, s). |
| 28 | 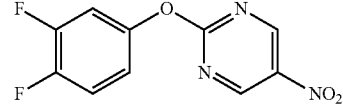 | NMR2; 6.93-7.02 (1H, m), 7.06-7.14 (1H, m), 7.23-7.32 (1H, m), 9.34 (2H, s). |
| 29 | 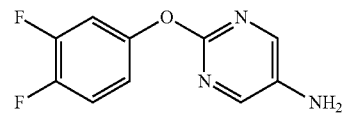 | NMR2; 3.56 (2H, brs), 6.87-6.95 (1H, m), 7.00-7.07 (1H, m), 7.12-7.22 (1H, m), 8.06 (2H, s). |
| 30 | 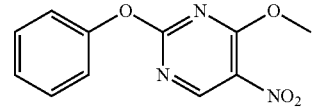 | NMR2; 4.09 (3H, s), 7.16-7.23 (2H, m), 7.28-7.36 (1H, m), 7.41-7.51 (2H, m), 9.08 (2H, s). |
| 31 | 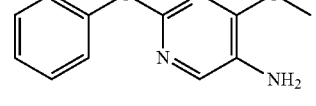 | NMR2; 3.45 (2H, brs), 4.03 (3H, s), 7.14-7.24 (3H, m), 7.34-7.43 (2H, m), 7.69 (2H, s). |
| 32 | 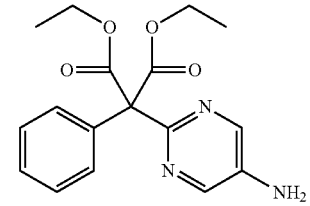 | NMR2; 1.26 (6H, t, J = 7.1 Hz), 3.73 (2H, brs), 4.32 (4H, q, J = 7.1 Hz), 7.24-7.34 (3H, m), 7.41-7.47 (2H, m), 8.18 (2H, s). |
| 33 | 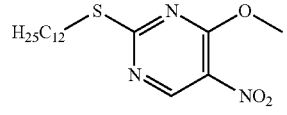 | NMR2: 0.85-0.91 (3H, m), 1.18-1.40 (16H, m), 1.40-1.51 (2H, m), 1.70-1.80 (2H, m), 3.18 (2H, t, J = 7.3 Hz), 4.17 (3H, s), 9.01 (1H, s). |
| 34 | 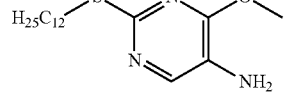 | NMR2: 0.85-0.91 (3H, m), 1.21-1.36 (16H, m), 1.35-1.49 (2H, m), 1.66-1.76 (2H, m), 3.08 (2H, t, J = 7.4 Hz), 3.48 (2H, brs), 4.01 (3H, s), 7.80 (1H, s). |
| 35 | 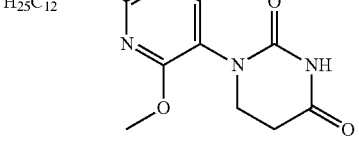 | NMR2: 0.84-0.91 (3H, m), 1.22-1.36 (16H, m), 1.36-1.49 (2H, m), 1.69-1.79 (2H, m), 2.84 (2H, t, J = 6.7 Hz), 3.12 (2H, t, J = 7.4 Hz), 3.68 (2H, t, J = 6.7 Hz), 4.03 (3H, s), 7.46 (1H, brs), 8.23 (1H, s). |
| 36 | 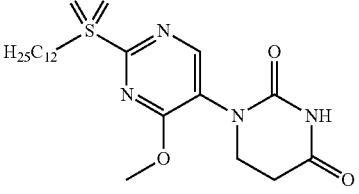 | NMR2: 0.84-0.92 (3H, m), 1.20-1.40 (16H, m), 1.40-1.53 (2H, m), 1.85-1.96 (2H, m), 2.89 (2H, t, J = 6.6 Hz), 3.46-3.55 (2H, m), 3.77 (2H, t, J = 6.6 Hz), 4.19 (3H, s), 7.52 (1H, brs), 8.61 (1H, s). |

EXAMPLES

Example 1

1-(2-Phenoxypyrimidin-5-yl)-5,6-dihydropyrimidine-2,4(1H,3H)-dione

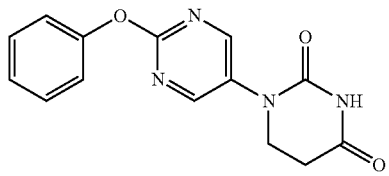 [SMILES: O=C1CCN(c2cnc(Oc3ccccc3)nc2)C(=O)N1]

2-Phenoxypyrimidine-5-amine (1.00 g) and acrylic acid (1.10 mL) were dissolved in toluene (10 mL), and stirred for 3 days at 80° C. The reaction solution was concentrated, the residue was dissolved in AcOH (10 mL), urea (642 mg) was added and the mixture was heated to reflux for 2 days. The reaction solution was concentrated, the crude product was purified by medium pressure preparative liquid chromatography (AcOEt/MeOH=1:0→9:1), and the resulting solid was washed with EtOH to obtain the object compound (233 mg).

NMR2: 2.90 (2H, t, J=6.7 Hz), 3.88 (2H, t, J=6.7 Hz), 7.17-7.24 (2H, m), 7.26-7.33 (1H, m), 7.40-7.49 (2H, m), 7.54 (1H, brs), 8.55 (2H, s).

Example 2

1-[2-(2-Fluorophenoxy)pyrimidin-5-yl]-5,6-dihydropyrimidine-2,4(1H,3H)-dione

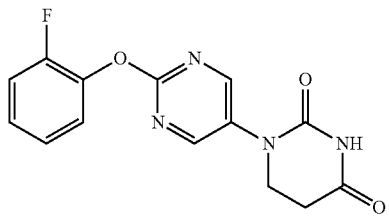

2-(2-Fluorophenoxy)pyrimidine-5-amine (1.00 g) and acrylic acid (0.67 mL) were dissolved in propionitrile (10 mL), and stirred for 2 days at 110° C. The reaction solution was concentrated, the residue was dissolved in AcOH (10 mL), urea (585 mg) was added, and the mixture was heated to reflux overnight. The reaction solution was concentrated, the crude product was purified by medium pressure preparative liquid chromatography (Hexane/AcOEt=1:1→0:1), and the resulting solid was washed with EtOH to obtain the object compound (289 mg).

NMR2: 2.90 (2H, t, J=6.7 Hz), 3.89 (2H, t, J=6.7 Hz), 7.12-7.34 (4H, m), 7.59 (1H, brs), 8.55 (2H, s).

Example 3

1-[2-(3-Fluorophenoxy)pyrimidin-5-yl]-5,6-dihydropyrimidine-2,4(1H,3H)-dione

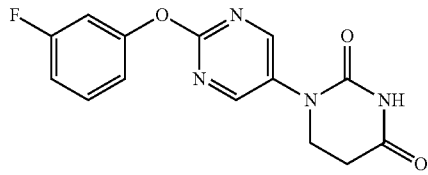 [SMILES: O=C1CCN(c2cnc(Oc3cccc(F)c3)nc2)C(=O)N1]

2-(3-Fluorophenoxy)pyrimidine-5-amine (500 mg) and acrylic acid (0.50 mL) were dissolved in toluene (2.5 mL), and stirred overnight at 80° C. The reaction solution was concentrated, the residue was dissolved in AcOH (2.5 mL), urea (293 mg) was added, and the mixture was heated to reflux for 2 days. The reaction solution was concentrated, the crude product was purified by medium pressure preparative liquid chromatography (DCM/AcOEt=4:1→1:1), and the resulting solid was washed with IPE to obtain the object compound (63 mg).

NMR2: 2.91 (2H, t, J=6.7 Hz), 3.90 (2H, t, J=6.7 Hz), 6.92-7.08 (3H, m), 7.34-7.48 (1H, m), 7.58 (1H, brs), 8.57 (2H, s).

Example 4

1-(2-Phenoxypyrimidin-5-yl)pyrimidine-2,4(1H,3H)-dione

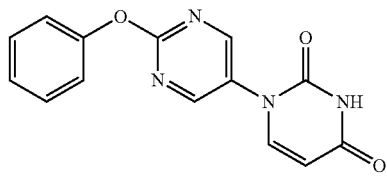 [SMILES: O=c1ccn(-c2cnc(Oc3ccccc3)nc2)c(=O)[nH]1]

1-[2-(Methylthio)pyrimidin-5-yl]pyrimidine-2,4(1H,3H)-dione (440 mg) was suspended in DCM (10 mL), aqueous 77% MCPBA (1002 mg) was added, and the mixture was stirred overnight at room temperature under a nitrogen atmosphere. Dimethyl sulfide was added to the reaction solution, which was then stirred and concentrated under reduced pressure, after which the residue was dissolved in DMF (4 mL), phenol (0.33 mL) and $K_2CO_3$ (772 mg) were added, and the mixture was stirred overnight at room temperature. This was then stirred for 3 hours at 70° C. Water was added to the reaction solution, which was then extracted with AcOEt. The organic layer was separated, washed with water and saturated saline, dried with sodium sulfate and concentrated to obtain a crude product. The crude product was purified by medium pressure preparative liquid chromatography (Hexane/AcOEt=1:1→0:1), and the resulting solid was washed with IPE and recrystallized from aqueous EtOH to obtain the object compound (270 mg).

NMR2: 5.93 (1H, dd, J=2.2 Hz, 8.0 Hz), 7.19-7.27 (3H, m), 7.27-7.35 (1H, m), 7.42-7.51 (2H, m), 8.46 (1H, brs), 8.59 (2H, s).

Example 5

1-[2-(3-Fluorophenoxy)pyrimidin-5-yl]-3-methyl-5,6-dihydropyrimidine-2,4(1H,3H)-dione

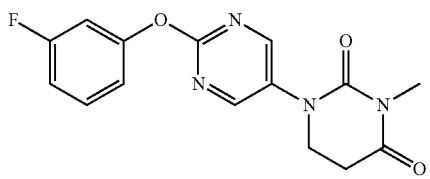 [SMILES: CN1C(=O)CCN(c2cnc(Oc3cccc(F)c3)nc2)C1=O]

1-[2-(3-Fluorophenoxy)pyrimidin-5-yl]-5,6-dihydropyrimidine-2,4(1H,3H)-dione (500 mg) and K₂CO₃ (343 mg) were suspended in DMF (5 ml), methyl iodide (0.11 mL) was added, and the mixture was stirred for 1 hour at 70° C. Water was added to the reaction solution, which was then extracted with AcOEt. The organic layer was separated, washed with water and saturated saline, dried with sodium sulfate, and concentrated to obtain the object compound (197 mg).

NMR2: 2.94 (2H, t, J=6.7 Hz), 3.25 (3H, s), 3.83 (2H, t, J=6.7 Hz), 6.92-7.08 (3H, m), 7.35-7.45 (1H, m), 8.55 (2H, s).

Example 6

1-[2-(3-Fluoro-2-methylphenoxy)pyrimidin-5-yl]-5,6-dihydropyrimidine-2,4(1H,3H)-dione

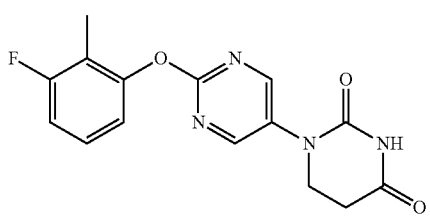 [SMILES: Cc1c(F)cccc1Oc1ncc(N2CCC(=O)NC2=O)cn1]

1-[2-(Dodecylsulfonyl)pyrimidin-5-yl]-5,6-dihydropyrimidine-2,4(1H,3H)-dione (500 mg), 3-fluoro-2-methylphenol (193 mg) and K₂CO₃ (244 mg) were suspended in DMF (7 mL), stirred at room temperature under a nitrogen atmosphere, and then stirred for 3 hours at 80° C. Water was added to the reaction solution, and the resulting solid was washed with water to obtain the object compound (143 mg).

NMR2: 2.12 (3H, d, J=1.8 Hz), 2.90 (2H, t, J=6.7 Hz), 3.89 (2H, t, J=6.7 Hz), 6.93 (1H, d, J=8.2 Hz), 6.95-7.03 (1H, m), 7.18-7.27 (1H, m), 7.61 (1H, brs), 8.55 (2H, s).

Example 7

1-[2-(3-Ethylphenoxy)pyrimidin-5-yl]-5,6-dihydropyrimidine-2,4(1H,3H)-dione

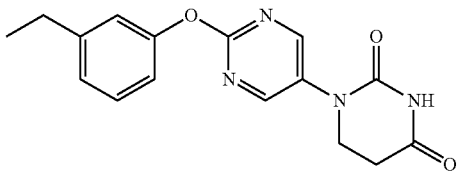 [SMILES: CCc1cccc(Oc2ncc(N3CCC(=O)NC3=O)cn2)c1]

1-[2-(3-Ethynylphenoxy)pyrimidin-5-yl]-5,6-dihydropyrimidine-2,4(1H,3H)-dione (312 mg) was dissolved in a mixed EtOH/THF (5/5 mL) solution, and aqueous 10% Pd/C (108 mg) was added and stirred for 3 hours under a hydrogen atmosphere. The reaction solution was filtered through Celite and washed with AcOEt, and the filtrate was concentrated to obtain a crude product. The crude product was purified by medium pressure preparative liquid chromatography (Hexane:AcOEt=1:1→0:1), and the resulting solid was washed with EtOH to obtain the object compound (99 mg).

NMR2: 1.26 (3H, t, J=7.6 Hz), 2.69 (2H, q, J=7.6 Hz), 2.90 (2H, t, J=6.7 Hz), 3.88 (2H, t, J=6.7 Hz), 6.97-7.08 (2H, m), 7.09-7.16 (1H, m), 7.35 (1H, t, J=7.8 Hz), 7.60 (1H, brs), 8.54 (2H, s).

Example 8

1-[2-(Phenylthio)pyrimidin-5-yl]-5,6-dihydropyrimidine-2,4(1H,3H)-dione

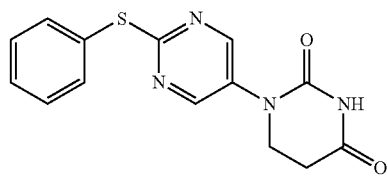

1-[2-(Methylsulfonyl)pyrimidin-5-yl]-5,6-dihydropyrimidine-2,4(1H,3H)-dione (224 mg), K₂CO₃ (172 mg) and thiophenol (0.10 mL) were suspended in DMF (5 mL), stirred at room temperature under a nitrogen atmosphere, and then stirred for 10 hours at 70° C. Water was added to the residue, which was then extracted with AcOEt. The organic layer was separated, washed with water and saturated saline, dried with sodium sulfate, and concentrated to obtain a crude product. The crude product was purified by medium pressure preparative liquid chromatography (Hexane:AcOEt=1:1→0:1), and then washed with EtOH to obtain the object compound (47 mg).

NMR2: 2.88 (2H, t, J=6.6 Hz), 3.85 (2H, t, J=6.6 Hz), 7.40-7.50 (3H, m), 7.58 (1H, brs). 7.60-7.68 (2H, m), 8.50 (2H, s).

The compounds of Examples 9 to 56 were each manufactured as in Examples 1 to 8. The structural formulae and physiochemical data for the compounds of the Examples 9 to 56 are each shown in Tables 2-1 to 2-6.

TABLE 2-1

| EX | STR | Data |
|---|---|---|
| 9 | 3-(trifluoromethyl)phenoxy pyrimidine dihydrouracil | NMR2; 2.91 (2H, t, J = 6.7 Hz), 3.90 (2H, t, J = 6.7 Hz), 7.37-7.45 (1H, m), 7.47-7.64 (4H, m), 8.57 (2H, s). |
| 10 | 3-(trifluoromethoxy)phenoxy pyrimidine dihydrouracil | NMR2; 2.91 (2H, t, J = 6.6 Hz), 3.90 (2H, t, J = 6.6 Hz), 7.07-7.22 (3H, m), 7.46 (1H, t, J = 8.3 Hz), 7.54 (1H, brs), 8.57 (2H, s). |
| 11 | 4-fluorophenoxy pyrimidine dihydrouracil | NMR2; 2.91 (2H, t, J = 6.7 Hz), 3.89 (2H, t, J = 6.7 Hz), 7.06-7.22 (4H, m), 7.48 (1H, brs), 8.55 (2H, s). |
| 12 | 2,4-difluorophenoxy pyrimidine dihydrouracil | NMR2; 2.90 (2H, t, J = 6.7 Hz), 3.90 (2H, t, J = 6.7 Hz), 6.90-7.02 (2H, m), 7.20-7.29 (1H, m), 7.54 (1H, brs), 8.55 (2H, s). |
| 13 | 2,6-difluorophenoxy pyrimidine dihydrouracil | NMR2; 2.90 (2H, t, J = 6.7 Hz), 3.90 (2H, t, J = 6.7 Hz), 6.98-7.08 (2H, m), 7.17-7.26 (1H, m), 7.54 (1H, brs), 8.56 (2H, s). |
| 14 | 3,5-difluorophenoxy pyrimidine dihydrouracil | NMR2; 2.92 (2H, t, J = 6.7 Hz), 3.91 (2H, t, J = 6.7 Hz), 6.70-6.85 (3H, m), 7.56 (1H, brs), 8.58 (2H, s). |
| 15 | 3,4-difluorophenoxy pyrimidine dihydrouracil | NMR2; 2.91 (2H, t, J = 6.7 Hz), 3.90 (2H, t, J = 6.7 Hz), 6.92-7.02 (1H, m), 7.04-7.14 (1H, m), 7.17-7.26 (1H, m), 7.56 (1H, brs), 8.56 (2H, s). |
| 16 | phenoxy pyrimidine methyl-dihydrouracil | NMR2; 1.35 (3H, d, J = 6.7 Hz), 2.63-2.73 (1H, m), 3.10 (1H, dd, J = 5.9 Hz, 16.7 Hz), 3.95-4.08 (1H, m), 7.17-7.25 (2H, m), 7.26-7.34 (1H, m), 7.41-7.52 (2H, m), 7.61 (1H, brs), 8.51 (1H, s). |

TABLE 2-2

| EX | STR | Data |
| --- | --- | --- |
| 17 | | NMR2 ; 0.94 (3H, t, J = 7.4 Hz), 1.61-1.84 (2H, m), 2.76-2.86 (1H, m), 3.06 (1H, dd, J = 6.2 Hz, 16.8 Hz), 3.72-3.82 (1H, m), 7.18-7.34 (3H, m), 7.41-7.50 (2H, m), 7.54 (1H, brs), 8.53 (2H, s). |
| 18 | | NMR2; 2.85 (2H, t, J = 6.7 Hz), 3.69 (2H, t, J = 6.7 Hz), 4.00 (3H, s), 7.17-7.24 (2H, m), 7.24-7.31 (1H, m), 7.37-7.50 (3H, m), 8.20 (1H, s). |
| 19 | | NMR2; 2.88 (2H, t, J = 6.7 Hz), 3.90 (2H, t, J = 6.7 Hz), 4.31 (2H, s), 7.20-7.40 (5H, m), 7.56 (1H, brs), 8.69 (2H, s). |
| 20 | | NMR2; 2.90 (2H, t, J = 6.7 Hz), 3.88 (2H, t, J = 6.7 Hz), 5.06 (2H, s), 6.79-6.86 (2H, m), 6.88-6.93 (1H, m), 7.30-7.46 (6H, m), 7.54 (1H, brs), 8.55 (2H, s). |
| 21 | | NMR2; 2.90 (2H, t, J = 6.7 Hz), 3.82 (3H, s), 3.88 (2H, t, J = 6.7 Hz), 6.73-6.87 (3H, m), 7.34 (1H, t, J = 8.2 Hz), 7.58 (1H, brs), 8.55 (2H, s). |
| 22 | | NMR2; 2.39 (3H, s), 2.90 (2H, t, J = 6.7 Hz), 3.88 (2H, t, J = 6.7 Hz), 6.96-7.05 (2H, m), 7.06-7.13 (1H, m), 7.32 (1H, t, J = 7.8 Hz), 7.66 (1H, brs), 8.54 (2H, s). |
| 23 | | NMR2; 2.91 (2H, t, J = 6.7 Hz), 3.90 (2H, t, J = 6.7 Hz), 7.33-7.39 (1H, m), 7.47-7.60 (4H, m), 8.57 (2H, s). |

TABLE 2-2-continued
| EX | STR | Data |
|---|---|---|
| 24 | 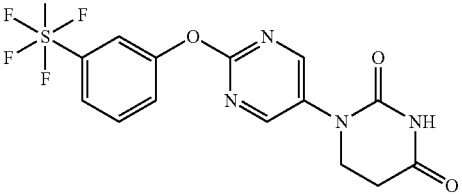 | NMR2; 2.91 (2H, t, J = 6.7 Hz), 3.91 (2H, t, J = 6.7 Hz), 7.36-7.42 (1H, m), 7.50-7.60 (2H, m), 7.62-7.72 (2H, m), 8.58 (2H, s). |
TABLE 2-3
| EX | STR | Data |
|---|---|---|
| 25 | 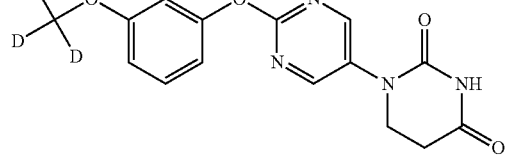 | NMR2; 2.90 (2H, t, J = 6.7 Hz), 3.88 (2H, t, J = 6.7 Hz), 6.72-6.87 (3H, m), 7.34 (1H, t, J = 8.2 Hz), 7.58 (1H, brs), 8.55 (2H, s). |
| 26 | 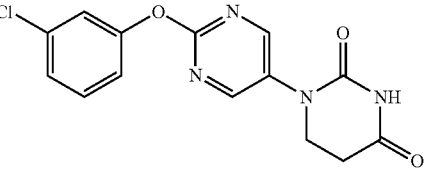 | NMR2; 2.91 (2H, t, J = 6.7 Hz), 3.90 (2H, t, J = 6.7 Hz), 7.08-7.14 (1H, m), 7.22-7.29 (2H, m), 7.37 (1H, t, J = 8.1 Hz), 7.56 (1H, brs), 8.56 (2H, s). |
| 27 | 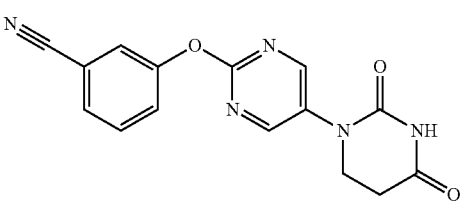 | NMR2; 2.92 (2H, t, J = 6.7 Hz), 3.91 (2H, t, J = 6.7 Hz), 7.43-7.62 (5H, m), 8.58 (2H, s). |
| 28 | 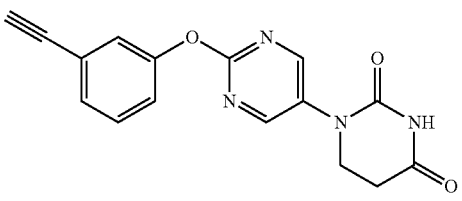 | NMR2; 2.91 (2H, t, J = 6.7 Hz), 3.11 (1H, s), 3.89 (2H, t, J = 6.7 Hz), 7.17-7.24 (1H, m), 7.32-7.35 (1H, m), 7.36-7.43 (2H, m), 7.63 (1H, brs), 8.56 (2H, s). |
| 29 | 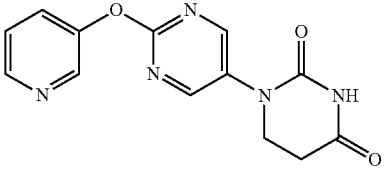 | NMR2; 2.91 (2H, t, J = 6.7 Hz), 3.90 (2H, t, J = 6.7 Hz), 7.37-7.43 (1H, m), 7.55-7.66 (2H, m), 8.54 (1H, dd, J = 1.4 Hz, 4.8 Hz), 8.55-8.60 (3H, m). |
| 30 | 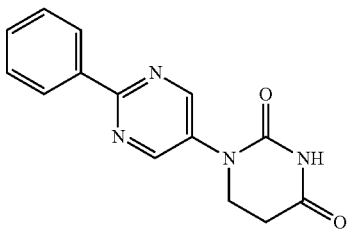 | NMR2; 2.93 (2H, t, J = 6.6 Hz), 3.99 (2H, t, J = 6.6 Hz), 7.46-7.54 (3H, m), 7.59 (1H, brs), 8.41-8.48 (2H, m), 8.83 (2H, s). |

TABLE 2-3-continued

| EX | STR | Data |
|---|---|---|
| 31 | | NMR2; 2.89 (2H, t, J = 6.7 Hz), 3.87 (2H, t, J = 6.7 Hz), 7.10-7.20 (1H, m), 7.33-7.46 (3H, m), 7.50 (1H, brs), 8.52 (2H, s). |
| 32 | | NMR2; 2.90 (2H, t, J = 6.7 Hz), 3.89 (2H, t, J = 6.7 Hz), 7.34 (1H, dd, J = 2.4 Hz, 8.9 Hz), 7.43-7.57 (3H, m), 7.65 (1H, d, J = 2.4 Hz), 7.80-7.90 (2H, m), 7.91 (1H, d, J = 8.9 Hz), 8.56 (2H, s). |

TABLE 2-4

| EX | STR | Data |
|---|---|---|
| 33 | | NMR2; 2.91 (2H, t, J = 6.7 Hz), 3.92 (2H, t, J = 6.7 Hz), 7.06-7.10 (1H, m), 7.25-7.29 (1H, m), 7.48 (1H, brs), 7.80 (1H, t, J = 7.9 Hz), 8.60 (2H, s). |
| 34 | | NMR2; 2.21 (3H, s), 2.90 (2H, t, J = 6.7 Hz), 3.88 (2H, t, J = 6.7 Hz), 7.07-7.14 (1H, m), 7.17-7.24 (1H, m), 7.24-7.34 (2H, m), 7.55 (1H, brs), 8.54 (2H, s). |
| 35 | | NMR2; 2.38 (3H, s), 2.90 (2H, t, J = 6.7 Hz), 3.87 (2H, t, J = 6.7 Hz), 7.05-7.12 (2H, m), 7.21-7.26 (2H, m), 7.60 (1H, brs), 8.54 (2H, s). |
| 36 | | NMR2; 2.16 (3H, s), 2.34 (3H, s), 2.89 (2H, t, J = 6.7 Hz), 3.88 (2H, t, J = 6.7 Hz), 6.98 (1H, d, J = 8.1 Hz), 7.03-7.13 (2H, m), 7.57 (1H, brs), 8.53 (2H, s). |
| 37 | | NMR2; 2.34 (6H, s), 2.90 (2H, t, J = 6.7 Hz), 3.88 (2H, t, J = 6.7 Hz), 6.78-6.84 (2H, m), 6.89-6.94 (1H, m), 7.50 (1H, brs), 8.54 (2H, s). |

TABLE 2-4-continued

| EX | STR | Data |
| --- | --- | --- |
| 38 | | NMR2; 2.16 (3H, s), 2.90 (2H, t, J = 6.7 Hz), 3.89 (2H, t, J = 6.7 Hz), 6.82-6.95 (2H, m), 7.21-7.27 (1H, m), 7.64 (1H, brs), 8.56 (2H, s). |
| 39 | | NMR2; 2.90 (2H, t, J = 6.7 Hz), 3.90 (2H, t, J = 6.7 Hz), 7.21-7.31 (2H, m), 7.33-7.40 (1H, m), 7.47-7.56 (2H, m), 8.56 (2H, s). |
| 40 | | NMR2; 2.90 (2H, t, J = 6.7 Hz), 3.89 (2H, t, J = 6.7 Hz), 7.11-7.19 (2H, m), 7.37-7.43 (2H, m), 7.68 (1H, brs), 8.55 (2H, s). |
| 41 | | NMR2; 5.94 (1H, dd, J = 2.2 Hz, 8.0 Hz), 6.95-7.08 (3H, m), 7.23-7.28 (1H, m), 7.38-7.46 (1H, m), 8.39 (1H, brs), 8.61 (2H, s). |

TABLE 2-5

| EX | STR | Data |
| --- | --- | --- |
| 42 | | NMR2; 2.85 (2H, t, J = 6.7 Hz), 3.70 (2H, t, J = 6.7 Hz), 4.00 (3H, s), 6.90-7.05 (3H, m), 7.33-7.44 (1H, m), 7.52 (1H, brs), 8.22 (1H, s). |
| 43 | | NMR2; 2.90 (2H, t, J = 6.7 Hz), 3.90 (2H, t, J = 6.7 Hz), 7.01-7.08 (1H, m), 7.21-(1H, dd, J = 1.5 Hz, 8.1 Hz), 7.40-7.48 (1H, m), 7.58 (1H, brs), 7.80 (1H, dd, J = 1.5 Hz, 7.9 Hz), 8.56 (2H, s). |
| 44 | | NMR2; 2.91 (2H, t, J = 6.7 Hz), 3.90 (2H, t, J = 6.7 Hz), 7.13-7.19 (1H, m), 7.31 (1H, t, J = 8.0 Hz), 7.37-7.45 (2H, m), 8.56 (2H, s). |

TABLE 2-5-continued

| EX | STR | Data |
|---|---|---|
| 45 | | NMR2; 2.90 (2H, t, J = 6.7 Hz), 3.88 (2H, t, J = 6.7 Hz), 7.13-7.23 (1H, m), 7.33-7.72 (9H, m), 8.56 (2H, s). |
| 46 | | NMR2; 2.84 (2H, t, J = 6.7 Hz), 3.78 (2H, t, J = 6.7 Hz), 7.18-7.56 (10H, m), 8.39 (2H, s). |
| 47 | | NMR2: 2.85 (2H, t, J = 6.7 Hz), 3.69 (2H, t, J = 6.7 Hz), 3.99 (3H, s), 7.17-7.34 (4H, m), 7.46 (1H, brs), 8.20 (1H, s). |
| 48 | | NMR2: 2.85 (2H, t, J = 6.7 Hz), 3.69 (2H, t, J = 6.7 Hz), 4.00 (3H, s), 7.06-7.20 (4H, m), 7.50 (1H, brs), 8.20 (1H, s). |
| 49 | | NMR2; 2.90 (2H, t, J = 6.7 Hz), 3.89 (2H, t, J = 6.7 Hz), 6.94-7.02 (2H, m), 7.64 (1H, brs), 7.72-7.78 (2H, m), 8.55 (2H, s). |

TABLE 2-6

| EX | STR | Data |
|---|---|---|
| 50 | | NMR2; 2.91 (2H, t, J = 6.7 Hz), 3.08 (1H, s), 3.89 (2H, t, J = 6.7 Hz), 7.13-7.21 (2H, m), 7.48-7.63 (3H, m), 8.56 (2H, s). |

TABLE 2-6-continued

| EX | STR | Data |
|---|---|---|
| 51 | 3-chlorophenoxy-4-methoxypyrimidine-dihydrouracil | NMR2: 2.85 (2H, t, J = 6.7 Hz), 3.69 (2H, t, J = 6.7 Hz), 4.01 (3H, s), 7.09-7.15 (1H, m), 7.22-7.29 (2H, m), 7.33-7.39 (1H, m), 7.49 (1H, brs), 8.22 (1H, s). |
| 52 | 2,6-difluorophenoxy-4-methoxypyrimidine-dihydrouracil | NMR2: 2.85 (2H, t, J = 6.7 Hz), 3.70 (2H, t, J = 6.7 Hz), 4.01 (3H, s), 6.98-7.08 (2H, m), 7.16-7.25 (1H, m), 7.44 (1H, brs), 8.21 (1H, s). |
| 53 | 2,4-difluorophenoxy-4-methoxypyrimidine-dihydrouracil | NMR2: 2.85 (2H, t, J = 6.7 Hz), 3.69 (2H, t, J = 6.7 Hz), 4.00 (3H, s), 6.88-7.01 (2H, m), 7.18-7.25 (1H, m), 7.45 (1H, brs), 8.20 (1H, s). |
| 54 | 3,5-difluorophenoxy-4-methoxypyrimidine-dihydrouracil | NMR2: 2.86 (2H, t, J = 6.7 Hz), 3.70 (2H, t, J = 6.7 Hz), 4.02 (3H, s), 6.70-6.85 (3H, m), 7.48 (1H, brs), 8.23 (1H, s). |
| 55 | 3-tert-butylphenoxy-pyrimidine-dihydrouracil | NMR1; 1.29 (9H, s), 2.74 (2H, t, J = 6.7 Hz), 3.82 (2H, t, J = 6.7 Hz), 6.99-7.02 (1H, m), 7.19-7.20 (1H, m), 7.28-7.30 (1H, m), 7.35-7.38 (1H, m), 8.64 (2H, s), 10.6 (1H, s). |
| 56 | 3-trimethylsilylphenoxy-pyrimidine-dihydrouracil | NMR1; 0.26 (9H, s), 2.74 (2H, t, J = 6.64 Hz), 3.82 (2H, t, J = 6.64 Hz), 7.18-7.21 (1H, m), 7.30 (1H, brd, J = 2.30 Hz), 7.39-7.47 (m, 2H), 8.64 (2H, s), 10.6 (1H, brs). |

TEST EXAMPLES

Pharmacological test results for typical compounds of the present invention are given below and the pharmacological actions of these compounds are explained, but the present invention is not limited by these test examples.

Test Example 1

Audiogenic Seizure Model

The animal model used in this test is a phenotype model for partial seizure (including secondary generalized seizure) and generalized tonic-clonic seizure, and has high clinical predictability. This test was performed in accordance with the report of De Sarro et al (Br J Pharmacol. 1988 February; 93(2): 247-56. Anticonvulsant effects of some calcium entry blockers in DBA/2 mice. De Sarro G B, Meldrum B S, Nistico G.).

In this test example, the example compounds shown in Table 3 below were used as test compounds. The following compound (compound of Example 5 of WO 2004/009559), which is the most similar compound when the substituent position is taken into consideration, was used as a comparative example compound.

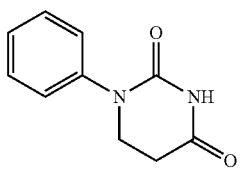 [SMILES: O=C1CCN(c2ccccc2)C(=O)N1]

The test compounds were suspended in 5% gum arabic/distilled water (w/v), and administered by forced oral administration to male and female DBA/2 mice (Japan SLC, Inc., 3 weeks old, 8 per group) at a dose of 30 mg/kg. After one hour of the oral administration of the test compound, each mouse was placed in a transparent acrylic cylinder 30 cm high and 23 cm in diameter, and 30 seconds were allowed for habituation. Then, they were exposed to auditory stimulation (12.6 kHz, 100-110 dB) for 1 minute or until a tonic seizure occurred.

The seizure response was assessed using the following scale, 0: no seizure, 1: wild running, 2: clonic seizure, 3: tonic seizure and 4: respiratory arrest. The maximum response was recorded as the seizure severity score.

The seizure suppression rate for each compound administration group was calculated according to the following formula.

$$\text{seizure suppression rate (\%)} = \left(1 - \frac{\text{seizure severity score of compound administration group}}{\text{seizure severity score of solvent administration group}}\right) \times 100 \quad [\text{Math. 1}]$$

The results are shown in Table 3.

TABLE 3

| EX | Seizure suppression rate (%) |
|---|---|
| 1 | 100 |
| 2 | 100 |
| 3 | 100 |
| 4 | 100 |
| 5 | 100 |
| 6 | 89 |
| 7 | 88 |
| 8 | 100 |
| 9 | 94 |
| 10 | 86 |
| 11 | 97 |
| 12 | 96 |
| 13 | 100 |
| 14 | 92 |
| 15 | 83 |
| 16 | 100 |
| 18 | 100 |
| 21 | 93 |
| 22 | 100 |
| 23 | 100 |
| 24 | 90 |
| 25 | 89 |
| 26 | 100 |
| 28 | 100 |
| 30 | 97 |
| 31 | 79 |
| 37 | 77 |
| 38 | 100 |
| 40 | 81 |
| 41 | 96 |
| 42 | 96 |
| 44 | 85 |
| 45 | 92 |
| 47 | 87 |
| 48 | 96 |
| 50 | 82 |
| 52 | 93 |
| 53 | 83 |
| 54 | 93 |
| 56 | 82 |
| Comparative Example* | 27** |

*Compound of Example 5 of WO 2004/009559
**A 10x dose (300 mg/kg) was required to reach a seizure suppression rate of 100%.

Test Example 2

Maximal Electroshock Seizure (MES) Model

This test is performed to evaluate the anticonvulsant activity of the compound. The mouse model used in this test is a phenotype model of generalized tonic-clonic seizure and secondary generalized partial seizure. This test was performed in accordance with the report of AJ Hill et al (Br J Pharmacol. 2012 December; 167(8): 1629-42. Cannabidivarin is anticonvulsant in mouse and rat, Hill A J, et al.).

In this test example, the compounds of Examples 1, 2, 3, 4, 5, 6, 7, 8, 9, 10, 11, 12, 13, 14, 15, 16, 18, 21, 22, 23, 24, 25, 26, 28, 30, 31, 37, 38, 40, 41, 42, 44, 45, 47, 48, 50, 52, 53, 54 and 56 were used as the test compounds.

The test compound was suspended in 5% gum arabic/distilled water (w/v), and administered by forced oral administration to male ICR mice (Japan SLC, Inc., 5 to 6 weeks old, 8 per group) at a dose of 30 mg/kg. After one hour of the oral administration of the test compound, the mice were stimulated by an application of electrical current (30 mA, 100 Hz, 0.2 second) through auricular electrodes using an electroconvulsive device (UGO BASILE SRL). Then, the incidence of tonic hindlimb extension seizure was recorded. In this test, tonic hindlimb extension seizures were induced in all mice of the solvent administration group, but the rate of seizure suppression was 75% or more with the example compounds 1, 2, 3, 5, 8, 10, 12, 13, 14, 16, 18, 22, 26, 28, 30, 31, 38, 42, 47, 48 and 54, and the suppression rate was 50% or more with the example compounds 4, 6, 9, 11, 23, 41 and 45.

Test Example 3

Subcutaneous Pentylenetetrazole (scPTZ) Model

This test is performed to evaluate the anticonvulsant activity of the compound as in Test Example 2. Unlike the phenotype of Test Example 2, the animal model used in this test is a phenotype model of generalized absence seizure and myoclonic seizure.

In this test example, the example compounds 1, 2, 3, 4, 5, 6, 7, 8, 9, 10, 11, 12, 13, 14, 15, 16, 18, 21, 22, 23, 24, 25, 26, 28, 30, 31, 37, 38, 40, 41, 42, 44, 45, 47, 48, 52, 53, 54, and 56 were used as the test compounds.

The test compound was suspended in 5% gum arabic/distilled water (w/v), and administered by forced oral administration to male ICR mice (Japan SLC, Inc., 5 to 6 weeks old, 10 per group) at a dose of 30 mg/kg. After 1 hour, 85 mg/kg of pentylenetetrazole dissolved in saline was administered subcutaneously, and the occurrence of clonic convulsions was evaluated for 30 minutes.

In this test, clonic convulsions were induced in all mice of the solvent administration group, but the rate of suppression against clonic convulsions was 75% or more with the example compounds 1, 2, 3, 4, 5, 11, 13, 14, 22, 23 and 28, and the suppression rate was 50% or more with the example compounds 12, 26, 41, 42, 44 and 56.

Test Example 4

Rotarod Test

This test is performed to evaluate the effect of the compound on the motor coordination.

The example compounds 1, 2, 3, 4, 5, 6, 7, 8, 9, 10, 11, 12, 13, 14, 15, 16, 18, 21, 22, 23, 24, 25, 26, 28, 30, 31, 37, 38, 40, 41, 42, 44, 45, 47, 48, 50, 52, 53, 54 and 56 were used as test compounds in this test.

Male ICR mice (Japan SLC, Inc., 5-6 weeks, 8 per group) were trained to remain on a fixed speed (15 rpm) rotating rod of rotarod apparatus (Muromachi Kikai Co., Ltd.) for 2 minutes. The test compound was suspended in 5% gum arabic/distilled water (w/v), and administered by forced oral administration at a dose of 30 mg/kg. After 1 hour of oral administration, the mice were again placed on the rod accelerated from 4 rpm to 40 rpm over 5 minutes and the latency to fall off the rod was recorded for 200 seconds. The falling latency of the compound administration group was calculated as a relative value relative to the average value of the falling latency in the solvent administration group.

In this test, the rate of motor dysfunction with the example compounds 1, 2, 3, 4, 6, 7, 8, 9, 10, 11, 12, 13, 14, 15, 16, 18, 21, 22, 23, 24, 25, 26, 28, 30, 31, 37, 38, 40, 41, 42, 44, 47, 48, 50, 52, 53, 54 and 56 was 25% or less.

INDUSTRIAL APPLICABILITY

Thus, since the compound of the present invention exhibits anticonvulsive action in all cases in multiple animal models used to evaluate antiepileptic drugs, it is useful as an antiepileptic drug with a wide treatment spectrum (compound for preventing and/or treating seizure in disease involving epileptic seizure or convulsive seizure (including multiple drug resistant seizure, refractory seizure, acute symptomatic seizure, febrile seizure and status epilepticus)). Moreover, the compound of the present invention is useful as a diagnostic compound for disease involving epileptic seizure or convulsive seizure (including multiple drug resistant seizure, refractory seizure, acute symptomatic seizure, febrile seizure and status epilepticus).

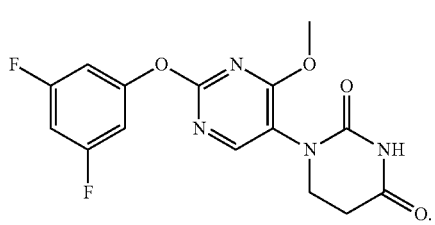

88. The compound according to claim 6, which is
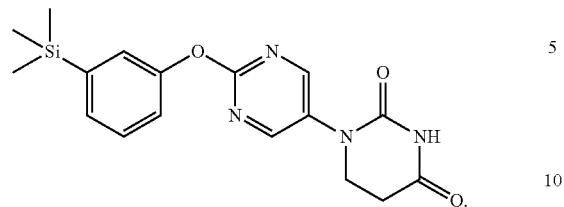

The invention claimed is:

1. A compound represented by Formula [I]:

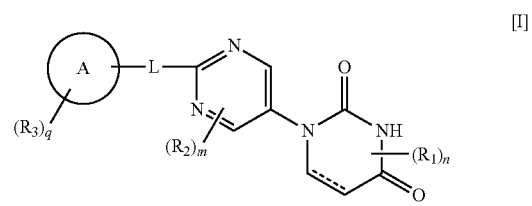

wherein
ring A is phenyl, naphthyl or pyridyl;
$R_1$ is lower alkyl;
$R_2$ is —O-lower alkyl;
$R_3$ is halogen, lower alkynyl, lower alkyl optionally substituted with halogen, —O-lower alkyl optionally substituted with deuterium or halogen, —S-lower alkyl optionally substituted with halogen, phenyl, pentafluorothio, —CN, —O-benzyl or —Si-mono-, di- or tri-lower alkyl wherein di or tri may be same or different alkyl;
L is bond, lower alkylene, —O— or —S—;
each of m and n is 0 or 1;
q is 0, 1 or 2, and when q is 2, each $R_3$ independently represents the same or different substituent; and
═════ represents single or double bond,
or a salt thereof.

2. The compound according to claim 1, wherein
ring A is phenyl,
L is —O—, and
n is 0, or a salt thereof.

3. The compound according to claim 1, wherein m is 0, or a salt thereof.

4. The compound according to claim 1, wherein $R_3$ is halogen, lower alkynyl, lower alkyl or —S-lower alkyl optionally substituted with halogen, or a salt thereof.

5. The compound according to claim 1, wherein

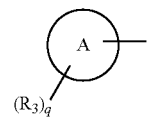

is phenyl, monohalophenyl, dihalophenyl, mono-lower alkynylphenyl or mono-lower alkylphenyl or phenyl substituted with one halogen and one lower alkyl group, or a salt thereof.

6. A compound selected from the group consisting of the following compounds:

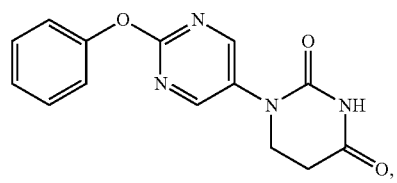

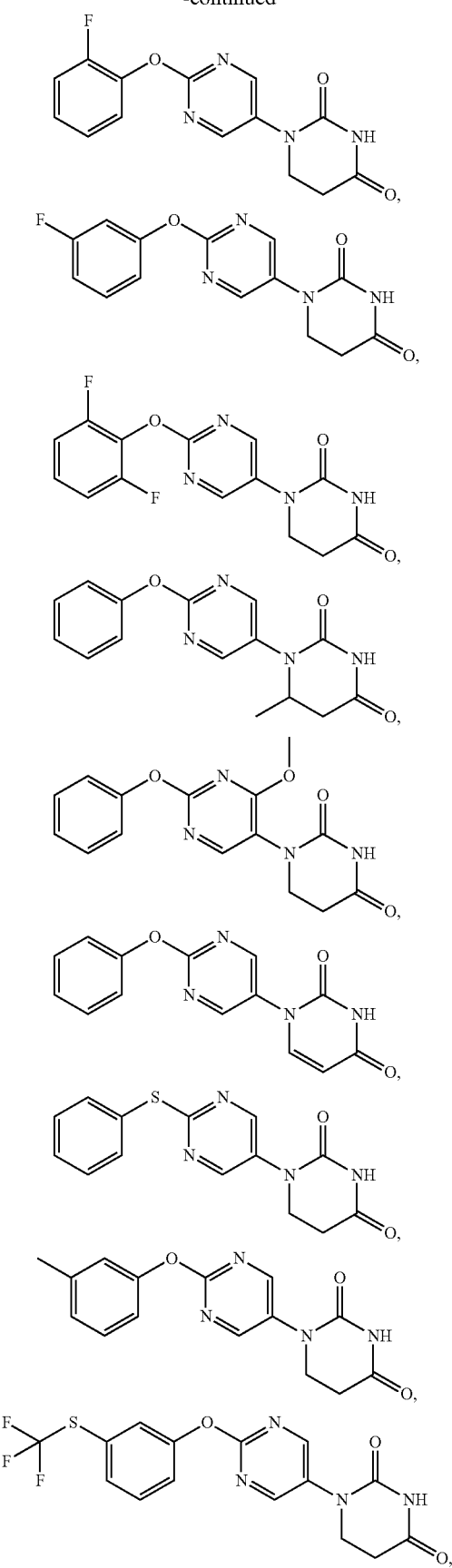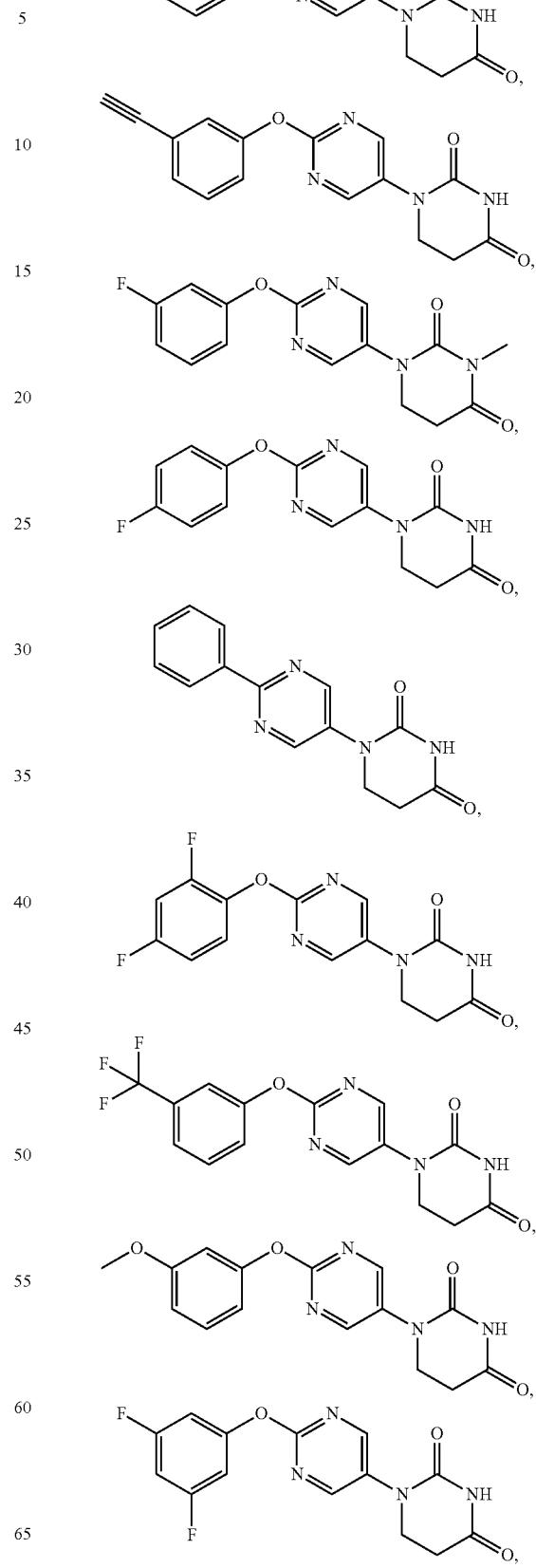

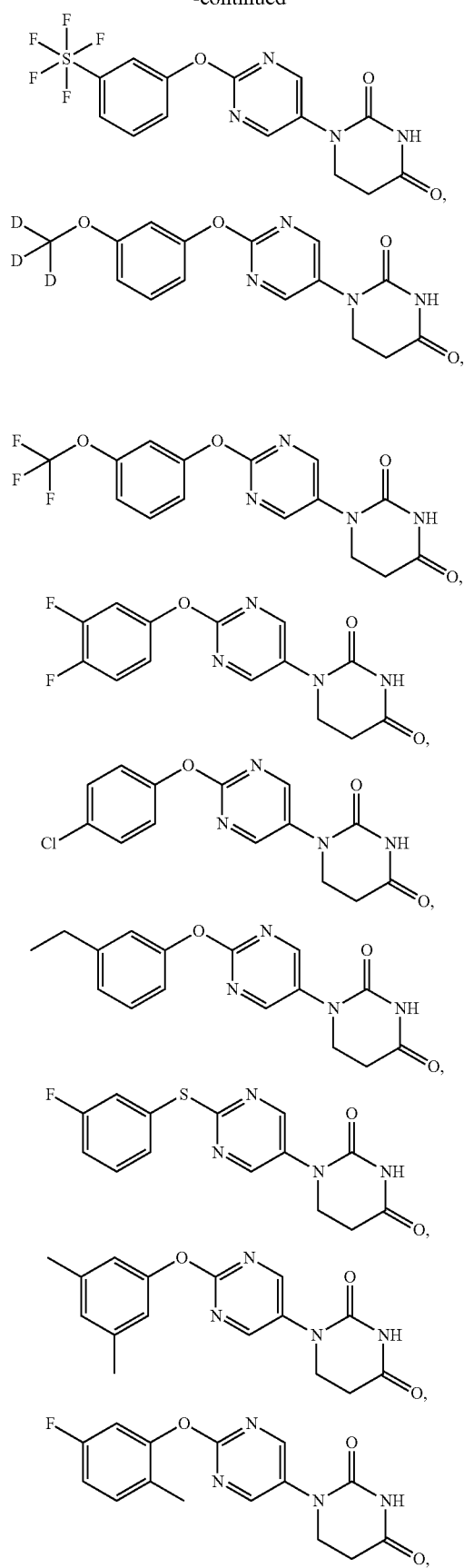
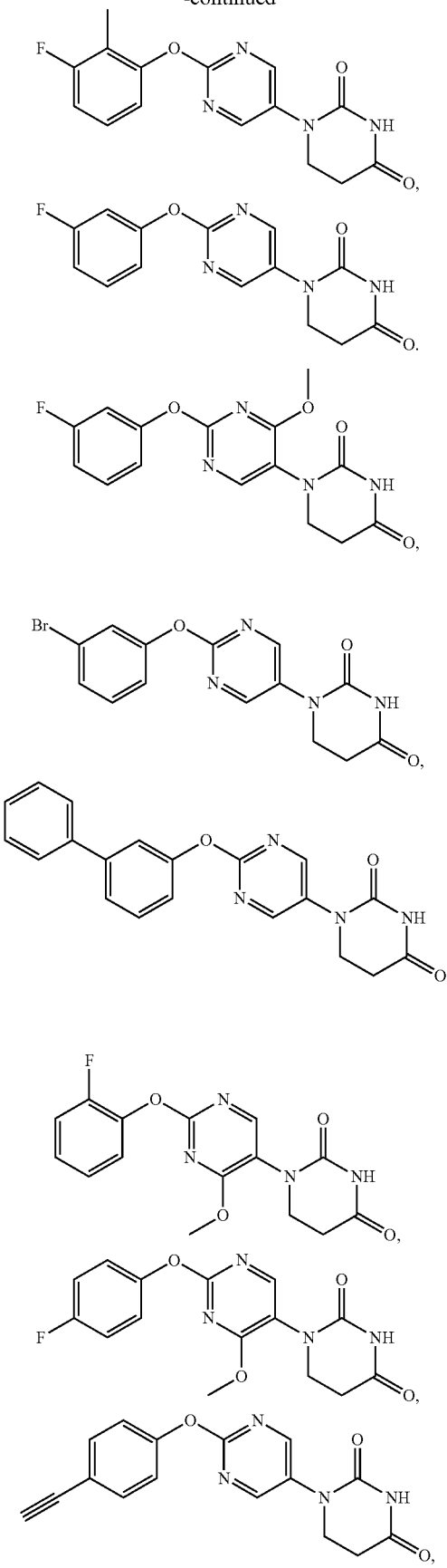

-continued

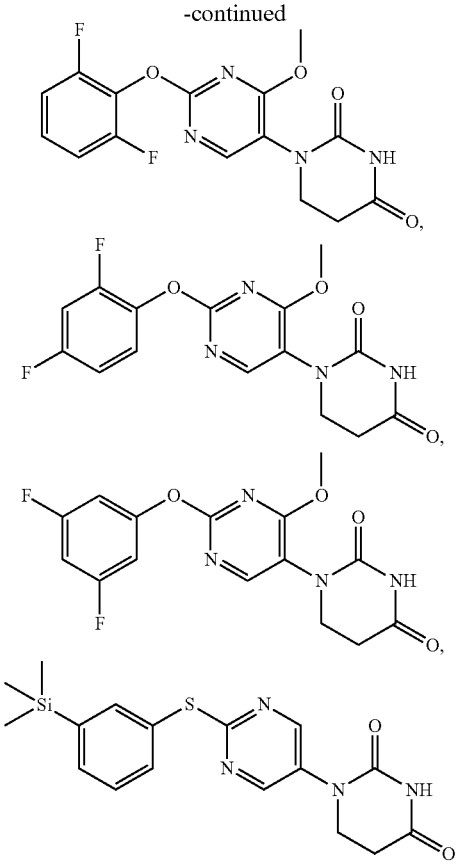

or a salt thereof.

7. A pharmaceutical composition comprising a compound according to claim 1 or a salt thereof, as an active ingredient and pharmaceutically acceptable carrier or excipient.

8. A method for treating seizure in diseases involving epileptic seizure or convulsive seizure (including multiple drug resistant seizure, refractory seizure, acute symptomatic seizure, febrile seizure and status epilepticus), which comprises administering to a human in need thereof an effective amount of a compound according to claim 1 or a salt thereof.

9. The compound according to claim 6, which is

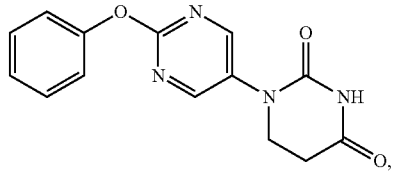

or a salt thereof.

10. The compound according to claim 6, which is

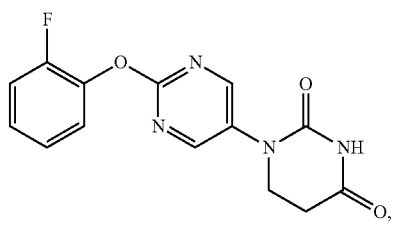 [SMILES: O=C1CCN(c2cnc(Oc3ccccc3F)nc2)C(=O)N1]

or a salt thereof.

11. The compound according to claim 6, which is

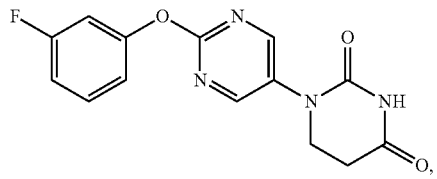 [SMILES: O=C1CCN(c2cnc(Oc3cccc(F)c3)nc2)C(=O)N1]

or a salt thereof.

12. The compound according to claim 6, which is

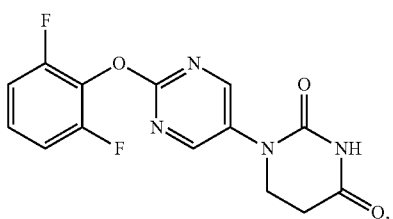

or a salt thereof.

13. The compound according to claim 6, which is

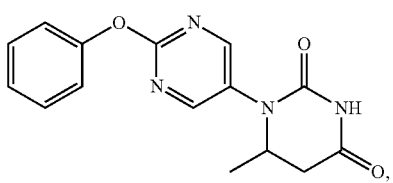 [SMILES: CC1CC(=O)NC(=O)N1c1cnc(Oc2ccccc2)nc1]

or a salt thereof.

14. The compound according to claim 6, which is

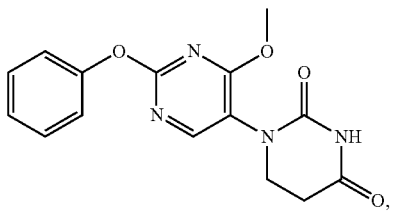 [SMILES: COc1nc(Oc2ccccc2)ncc1N1CCC(=O)NC1=O]

or a salt thereof.

15. The compound according to claim 6, which is

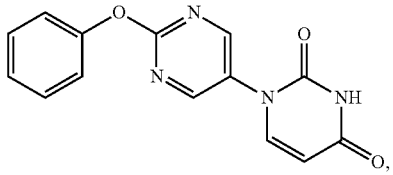 [SMILES: O=c1ccn(-c2cnc(Oc3ccccc3)nc2)c(=O)[nH]1]

or a salt thereof.

16. The compound according to claim 6, which is

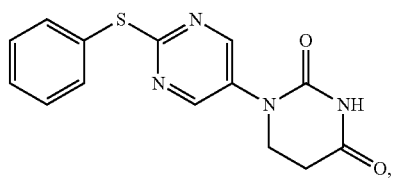

or a salt thereof.

17. The compound according to claim 6, which is

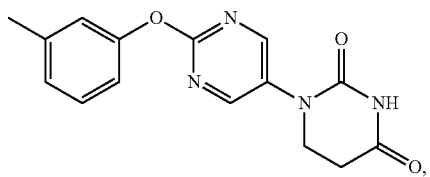

or a salt thereof.

18. The compound according to claim 6, which is

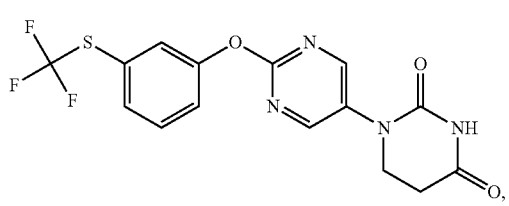

or a salt thereof.

19. The compound according to claim 6, which is

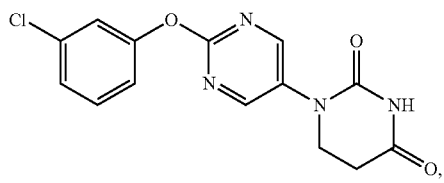 [SMILES: O=C1CCN(c2cnc(Oc3cccc(Cl)c3)nc2)C(=O)N1]

or a salt thereof.

20. The compound according to claim 6, which is

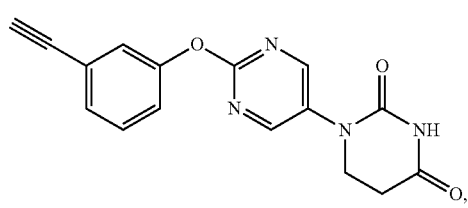 [SMILES: C#Cc1cccc(Oc2ncc(N3CCC(=O)NC3=O)cn2)c1]

or a salt thereof.

21. The compound according to claim 6, which is

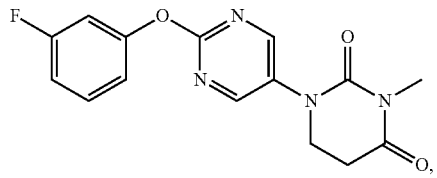 [SMILES: CN1C(=O)CCN(c2cnc(Oc3cccc(F)c3)nc2)C1=O]

or a salt thereof.

22. The compound according to claim 6, which is

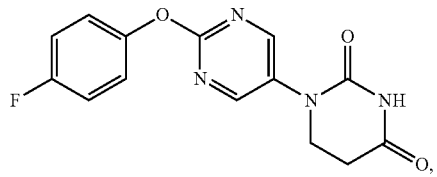 [SMILES: O=C1CCN(c2cnc(Oc3ccc(F)cc3)nc2)C(=O)N1]

or a salt thereof.

23. The compound according to claim 6, which is

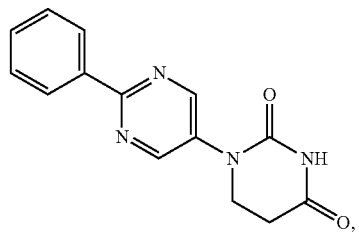 [SMILES: O=C1CCN(c2cnc(-c3ccccc3)nc2)C(=O)N1]

or a salt thereof.

24. The compound according to claim 6, which is

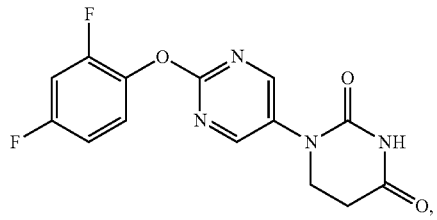

or a salt thereof.

25. The compound according to claim 6, which is

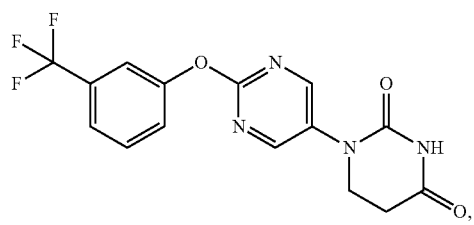 [SMILES: O=C1CCN(c2cnc(Oc3cccc(C(F)(F)F)c3)nc2)C(=O)N1]

or a salt thereof.

26. The compound according to claim 6, which is

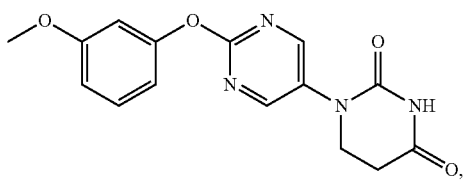 [SMILES: COc1cccc(Oc2ncc(N3CCC(=O)NC3=O)cn2)c1]

or a salt thereof.

27. The compound according to claim 6, which is

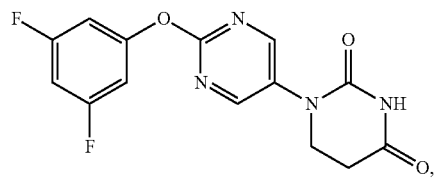 [SMILES: O=C1CCN(c2cnc(Oc3cc(F)cc(F)c3)nc2)C(=O)N1]

or a salt thereof.

28. The compound according to claim 6, which is

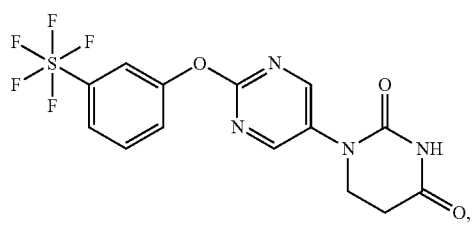 [SMILES: O=C1CCN(c2cnc(Oc3cccc(S(F)(F)(F)(F)F)c3)nc2)C(=O)N1]

or a salt thereof.

29. The compound according to claim 6, which is

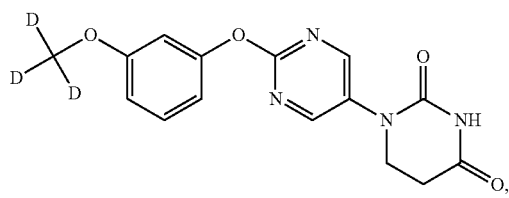

or a salt thereof.

30. The compound according to claim 6, which is

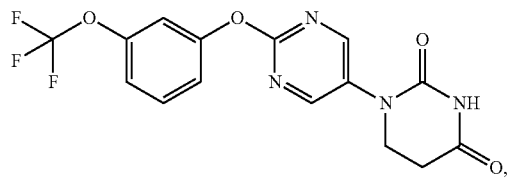 [SMILES: O=C1CCN(c2cnc(Oc3cccc(OC(F)(F)F)c3)nc2)C(=O)N1]

or a salt thereof.

31. The compound according to claim 6, which is

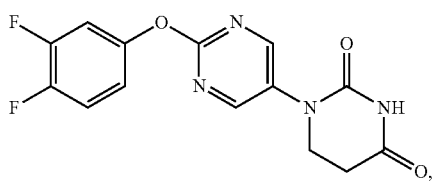

or a salt thereof.

32. The compound according to claim 6, which is

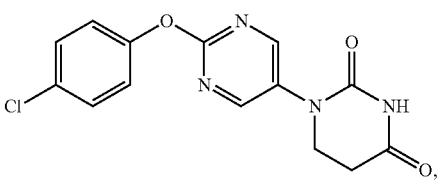 [SMILES: O=C1CCN(c2cnc(Oc3ccc(Cl)cc3)nc2)C(=O)N1]

or a salt thereof.

33. The compound according to claim 6, which is

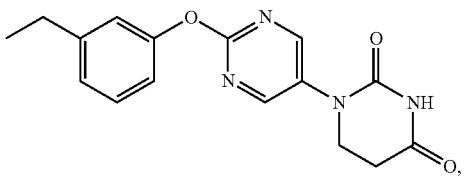 [SMILES: CCc1cccc(Oc2ncc(N3CCC(=O)NC3=O)cn2)c1]

or a salt thereof.

34. The compound according to claim 6, which is

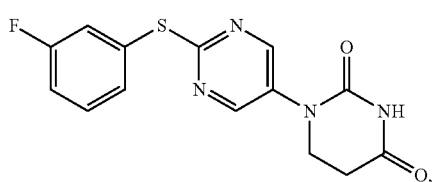

or a salt thereof.

35. The compound according to claim 6, which is

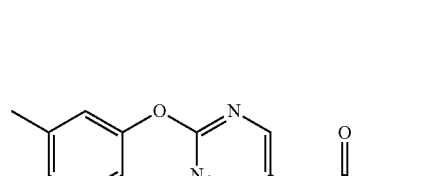

or a salt thereof.

36. The compound according to claim 6, which is

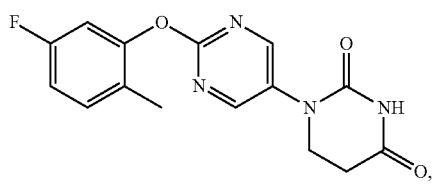 [SMILES: Cc1ccc(F)cc1Oc1ncc(N2CCC(=O)NC2=O)cn1]

or a salt thereof.

37. The compound according to claim 6, which is

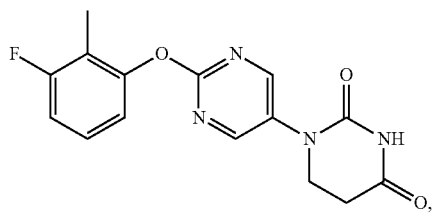 [SMILES: Cc1c(F)cccc1Oc1ncc(N2CCC(=O)NC2=O)cn1]

or a salt thereof.

38. The compound according to claim 6, which is

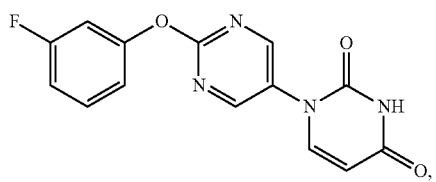 [SMILES: O=c1ccn(-c2cnc(Oc3cccc(F)c3)nc2)c(=O)[nH]1]

or a salt thereof.

39. The compound according to claim 6, which is

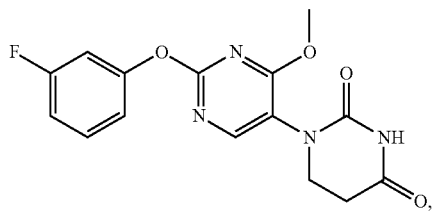 [SMILES: COc1nc(Oc2cccc(F)c2)ncc1N1CCC(=O)NC1=O]

or a salt thereof.

40. The compound according to claim 6, which is

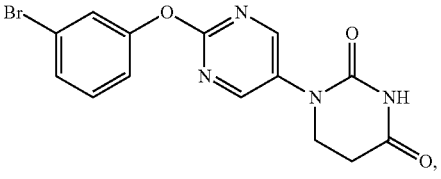

or a salt thereof.

41. The compound according to claim 6, which is

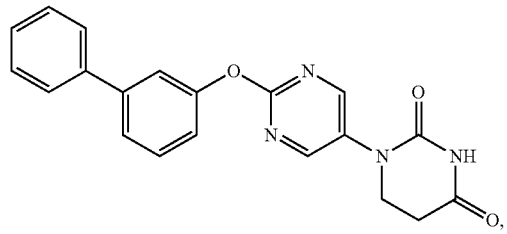 [SMILES: O=C1CCN(c2cnc(Oc3cccc(-c4ccccc4)c3)nc2)C(=O)N1]

or a salt thereof.

42. The compound according to claim 6, which is

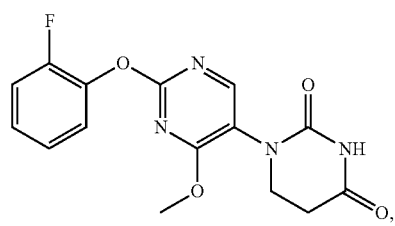 [SMILES: COc1nc(Oc2ccccc2F)ncc1N1CCC(=O)NC1=O]

or a salt thereof.

43. The compound according to claim 6, which is

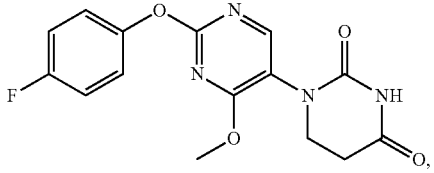 [SMILES: COc1nc(Oc2ccc(F)cc2)ncc1N1CCC(=O)NC1=O]

or a salt thereof.

44. The compound according to claim 6, which is

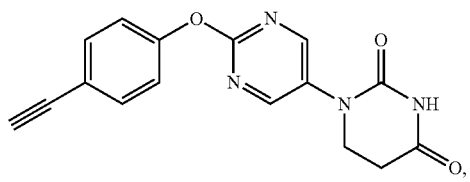 [SMILES: C#Cc1ccc(Oc2ncc(N3CCC(=O)NC3=O)cn2)cc1]

or a salt thereof.

45. The compound according to claim 6, which is

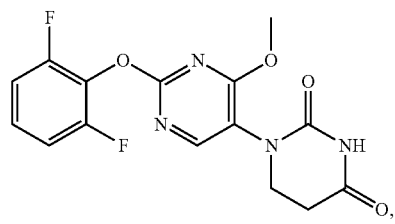

or a salt thereof.

46. The compound according to claim 6, which is

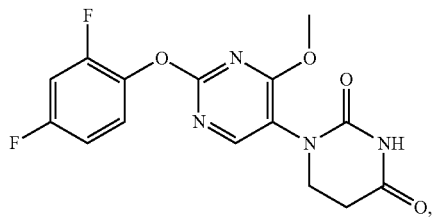 [SMILES: COc1nc(Oc2ccc(F)cc2F)ncc1N1CCC(=O)NC1=O]

or a salt thereof.

47. The compound according to claim 6, which is

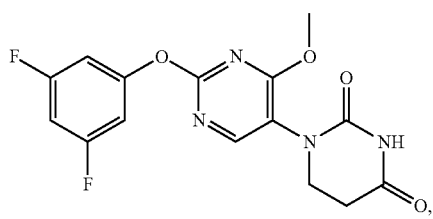 [SMILES: COc1nc(Oc2cc(F)cc(F)c2)ncc1N1CCC(=O)NC1=O]

or a salt thereof.

48. The compound according to claim 6, which is

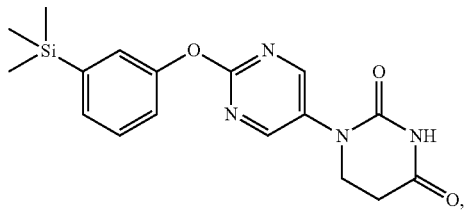 [SMILES: C[Si](C)(C)c1cccc(Oc2ncc(N3CCC(=O)NC3=O)cn2)c1]

or a salt thereof.

49. The compound according to claim 6, which is

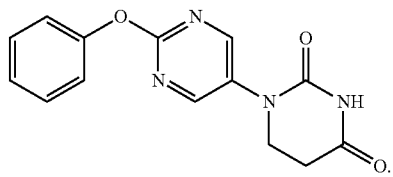

50. The compound according to claim 6, which is

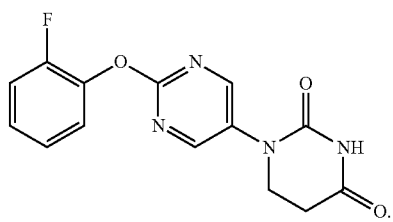 [SMILES: O=C1CCN(c2cnc(Oc3ccccc3F)nc2)C(=O)N1]

51. The compound according to claim 6, which is

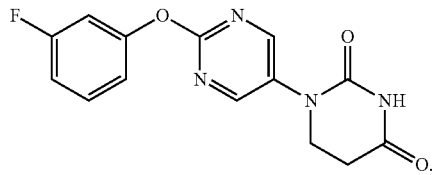 [SMILES: O=C1CCN(c2cnc(Oc3cccc(F)c3)nc2)C(=O)N1]

52. The compound according to claim 6, which is

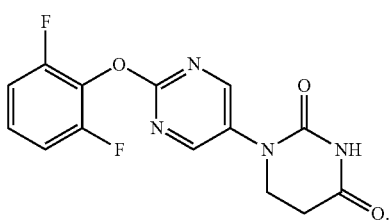 [SMILES: O=C1CCN(c2cnc(Oc3c(F)cccc3F)nc2)C(=O)N1]

53. The compound according to claim 6, which is

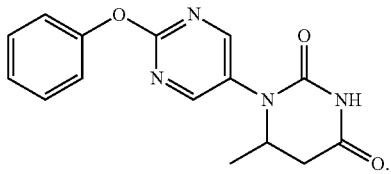 [SMILES: CC1CC(=O)NC(=O)N1c1cnc(Oc2ccccc2)nc1]

54. The compound according to claim 6, which is

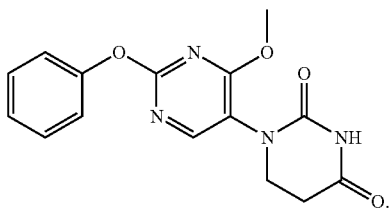 [SMILES: COc1nc(Oc2ccccc2)ncc1N1CCC(=O)NC1=O]

55. The compound according to claim 6, which is

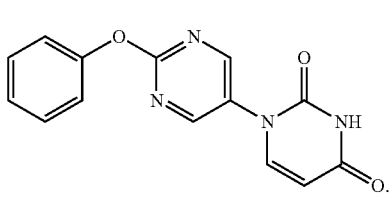 [SMILES: O=c1ccn(-c2cnc(Oc3ccccc3)nc2)c(=O)[nH]1]

56. The compound according to claim 6, which is

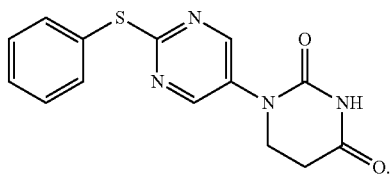 [SMILES: O=C1CCN(c2cnc(Sc3ccccc3)nc2)C(=O)N1]

57. The compound according to claim 6, which is

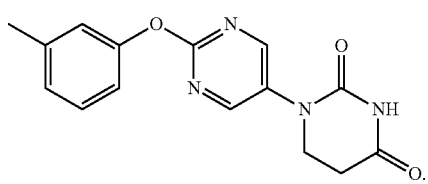 [SMILES: Cc1cccc(Oc2ncc(N3CCC(=O)NC3=O)cn2)c1]

58. The compound according to claim 6, which is

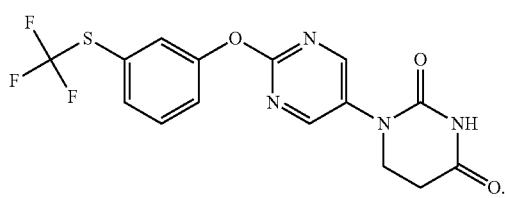 [SMILES: O=C1CCN(c2cnc(Oc3cccc(SC(F)(F)F)c3)nc2)C(=O)N1]

59. The compound according to claim 6, which is

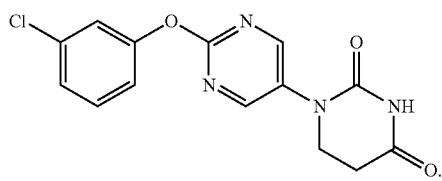 [SMILES: O=C1CCN(c2cnc(Oc3cccc(Cl)c3)nc2)C(=O)N1]

60. The compound according to claim 6, which is

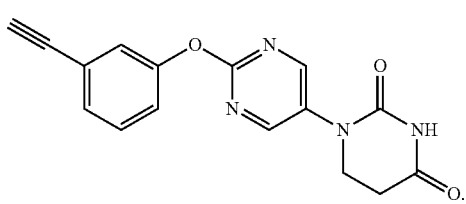 [SMILES: C#Cc1cccc(Oc2ncc(N3CCC(=O)NC3=O)cn2)c1]

61. The compound according to claim 6, which is

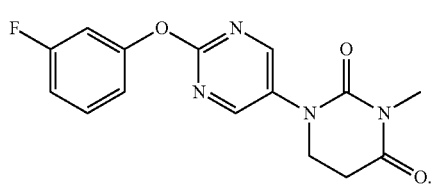 [SMILES: CN1C(=O)CCN(c2cnc(Oc3cccc(F)c3)nc2)C1=O]

62. The compound according to claim 6, which is

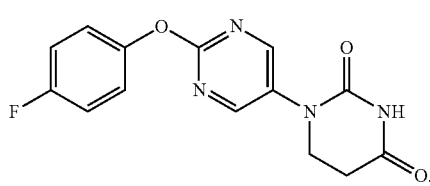 [SMILES: O=C1CCN(c2cnc(Oc3ccc(F)cc3)nc2)C(=O)N1]

63. The compound according to claim 6, which is

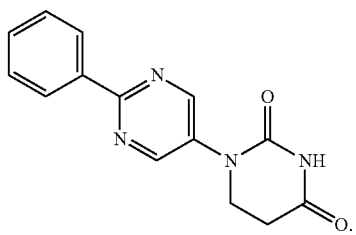 [SMILES: O=C1CCN(c2cnc(-c3ccccc3)nc2)C(=O)N1]

64. The compound according to claim 6, which is

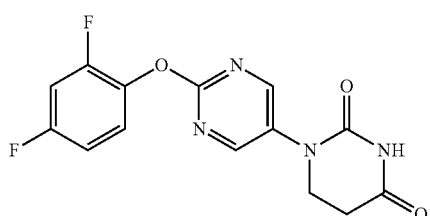

65. The compound according to claim 6, which is

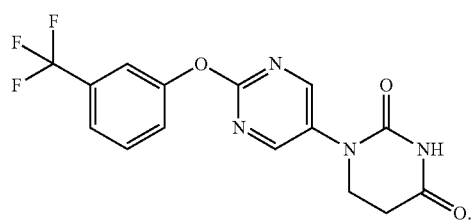 [SMILES: O=C1CCN(c2cnc(Oc3cccc(C(F)(F)F)c3)nc2)C(=O)N1]

66. The compound according to claim 6, which is

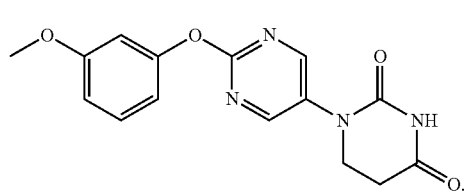

67. The compound according to claim 6, which is

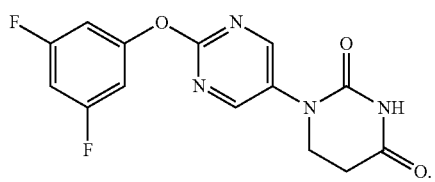 [SMILES: O=C1CCN(c2cnc(Oc3cc(F)cc(F)c3)nc2)C(=O)N1]

68. The compound according to claim 6, which is

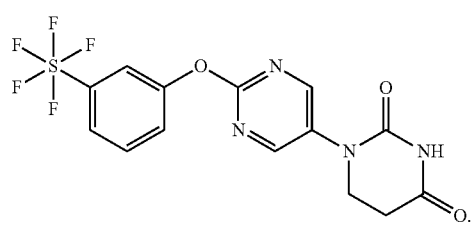 [SMILES: O=C1CCN(c2cnc(Oc3cccc(S(F)(F)(F)(F)F)c3)nc2)C(=O)N1]

69. The compound according to claim 6, which is

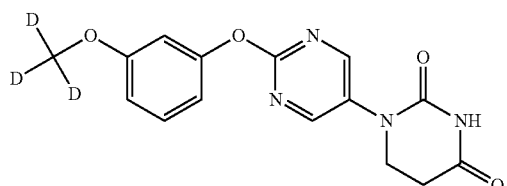

70. The compound according to claim 6, which is

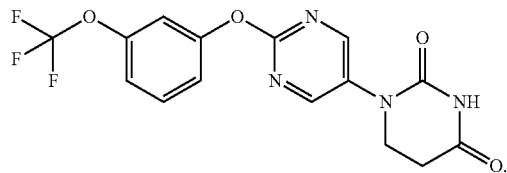 [SMILES: O=C1CCN(c2cnc(Oc3cccc(OC(F)(F)F)c3)nc2)C(=O)N1]

71. The compound according to claim 6, which is

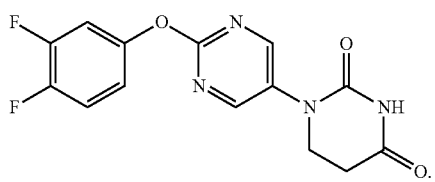 [SMILES: O=C1CCN(c2cnc(Oc3ccc(F)c(F)c3)nc2)C(=O)N1]

72. The compound according to claim 6, which is

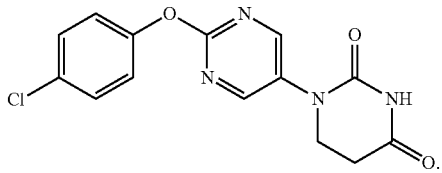 [SMILES: O=C1CCN(c2cnc(Oc3ccc(Cl)cc3)nc2)C(=O)N1]

73. The compound according to claim 6, which is

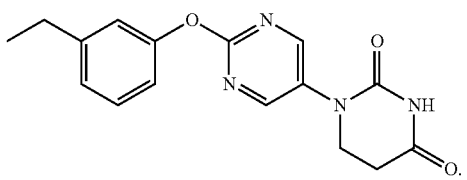 [SMILES: CCc1cccc(Oc2ncc(N3CCC(=O)NC3=O)cn2)c1]

74. The compound according to claim 6, which is

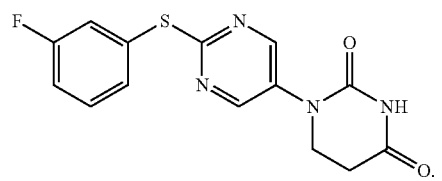

75. The compound according to claim 6, which is

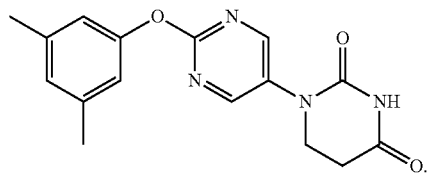

76. The compound according to claim 6, which is

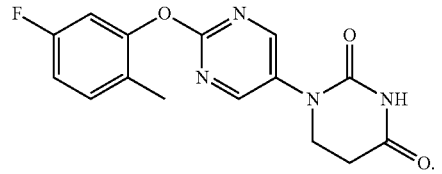 [SMILES: Cc1ccc(F)cc1Oc1ncc(N2CCC(=O)NC2=O)cn1]

77. The compound according to claim 6, which is

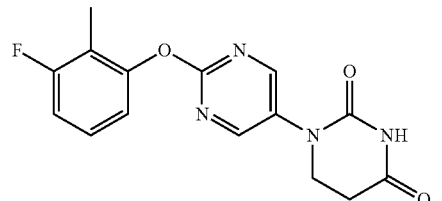

78. The compound according to claim 6, which is

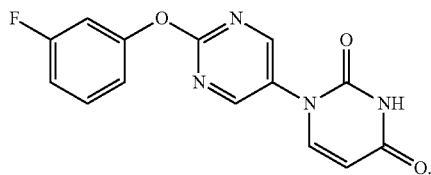

79. The compound according to claim 6, which is

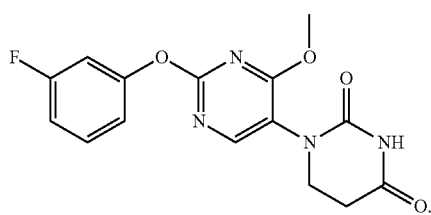 [SMILES: COc1nc(Oc2cccc(F)c2)ncc1N1CCC(=O)NC1=O]

80. The compound according to claim 6, which is

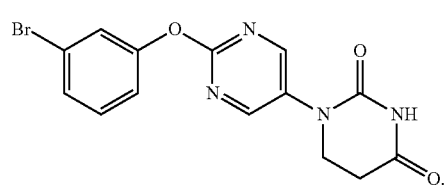

81. The compound according to claim 6, which is

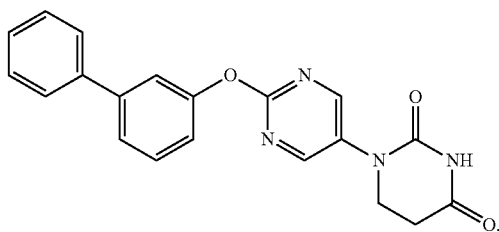 [SMILES: O=C1CCN(c2cnc(Oc3cccc(-c4ccccc4)c3)nc2)C(=O)N1]

82. The compound according to claim 6, which is

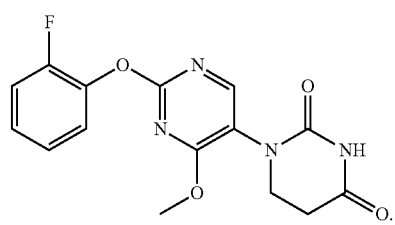 [SMILES: COc1nc(Oc2ccccc2F)ncc1N1CCC(=O)NC1=O]

83. The compound according to claim 6, which is

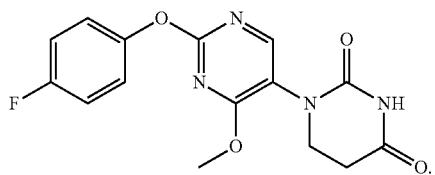 [SMILES: COc1nc(Oc2ccc(F)cc2)ncc1N1CCC(=O)NC1=O]

84. The compound according to claim 6, which is

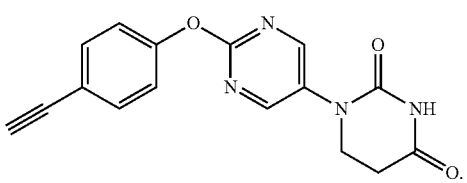 [SMILES: C#Cc1ccc(Oc2ncc(N3CCC(=O)NC3=O)cn2)cc1]

85. The compound according to claim 6, which is

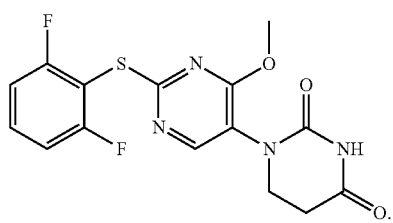 [SMILES: COc1nc(Sc2c(F)cccc2F)ncc1N1CCC(=O)NC1=O]

86. The compound according to claim 6, which is

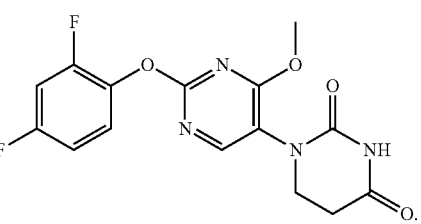

87. The compound according to claim 6, which is